US008921382B2

(12) United States Patent
Brewster et al.

(10) Patent No.: US 8,921,382 B2
(45) Date of Patent: Dec. 30, 2014

(54) THIAZOLO[5,4-D] PYRIMIDINES AND THEIR USE AS AGROCHEMICALS

(75) Inventors: William K. Brewster, Indianapolis, IN (US); Carla J. R. Klittich, Zionsville, IN (US); Brent J. Rieder, Greenfield, IN (US); Thomas L. Siddall, Zionsville, IN (US); Chenglin Yao, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 323 days.

(21) Appl. No.: 12/985,772

(22) Filed: Jan. 6, 2011

(65) Prior Publication Data
US 2011/0166164 A1 Jul. 7, 2011

Related U.S. Application Data

(60) Provisional application No. 61/293,014, filed on Jan. 7, 2010.

(51) Int. Cl.
C07D 513/04 (2006.01)
A01N 43/90 (2006.01)
A61K 31/519 (2006.01)

(52) U.S. Cl.
CPC .............. *C07D 513/04* (2013.01); *A01N 43/90* (2013.01); *A61K 31/519* (2013.01)
USPC ........................................ 514/260.1; 544/255

(58) Field of Classification Search
CPC ............................... C07D 513/04; A01N 43/54
USPC ........................................ 544/255; 514/260.1
See application file for complete search history.

(56) References Cited

U.S. PATENT DOCUMENTS

| | | | |
|---|---|---|---|
| 3,309,359 | A | 3/1967 | Duschinsky et al. |
| 3,368,938 | A | 2/1968 | Berger et al. |
| 3,868,373 | A | 2/1975 | Hoffer |
| 4,845,081 | A | 7/1989 | Sloan |
| 4,996,208 | A | 2/1991 | Lindner et al. |
| 5,034,393 | A | 7/1991 | Hackler et al. |
| 5,326,766 | A | 7/1994 | Dreikorn et al. |
| 5,350,749 | A | 9/1994 | Hackler et al. |
| 5,962,489 | A | 10/1999 | Mueller et al. |
| 6,066,638 | A | 5/2000 | Bereznak et al. |
| 6,448,262 | B1 | 9/2002 | Wood |
| 6,617,330 | B2 | 9/2003 | Walter |
| 7,914,799 | B2 | 3/2011 | Jira et al. |
| 2003/0039667 | A1 | 2/2003 | Jira et al. |
| 2008/0004253 | A1 | 1/2008 | Branstetter et al. |
| 2008/0269238 | A1 | 10/2008 | Sugihara et al. |
| 2009/0203647 | A1 | 8/2009 | Benko et al. |
| 2010/0022538 | A1 | 1/2010 | Boebel et al. |
| 2011/0034493 | A1 | 2/2011 | Boebel et al. |

FOREIGN PATENT DOCUMENTS

| | | |
|---|---|---|
| EP | 0102908 A1 | 3/1984 |
| EP | 0139613 A1 | 5/1985 |
| EP | 0332579 A2 | 9/1989 |
| EP | 0414386 A1 | 2/1991 |
| EP | 0877022 B1 | 4/2003 |
| GB | 1461184 A | 1/1977 |
| JP | AH0366689 | 3/1991 |
| JP | 6001793 A | 1/1994 |
| WO | WO94/04526 | 3/1994 |
| WO | W09733890 A1 | 9/1997 |
| WO | 03039258 | 5/2003 |
| WO | 2007046809 | 4/2007 |
| WO | WO2009/094442 A2 | 7/2009 |
| WO | WO2010047866 A2 | 4/2010 |
| WO | WO2010085377 A2 | 7/2010 |

OTHER PUBLICATIONS

Inoue et al. (Chemical & Pharmaceutical Bulletin, 1958, 6, pp. 352-355).*
Marchal et al. (Bulletin des Societes Chimiques Belges, 1960, 69, pp. 177-193).*
International Search Report and Written Opinion for PCT/US2012/050930, Oct. 15, 2012.
International Search Report for PCT/US2010/044579, Sep. 21, 2010.
Chiacchio U, et al. Enantioselective Syntheses and Cytotoxicity of N,O-Nucleosides. Journal of Medicinal Chemistry, Jan. 1, 2003, vol. 46, pp. 3696-3702.
Morris J Robins, et al. A direct synthesis of 5-fluorocytosine and its nucleosides using trifluoromethyl hypofluorite. Journal of the Chemical Society, Chemical Communications, No. 1, Jan. 1, 1972, p. 18.

(Continued)

*Primary Examiner* — Susanna Moore
(74) *Attorney, Agent, or Firm* — CW Arnett; Faegre Baker Daniels, LLP

(57) ABSTRACT

The present disclosure relates to thiazolo[5,4-d]pyrimidines and their use as agrochemicals and animal health products. In some embodiments, the disclosure relates to compounds of the formula (I-A) and of the formula (I-B):

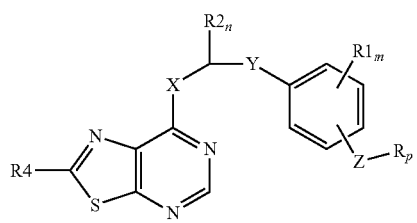

I-A

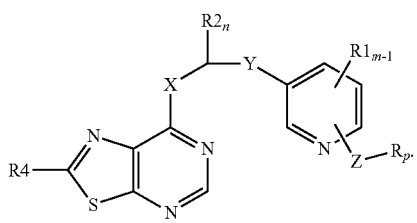

I-B

20 Claims, No Drawings

(56) References Cited

OTHER PUBLICATIONS

Arthur F. Lewis et al. Synthesis and in vitro anti-human cytomegalovirus (hcmv) activity of certain alkenyl substituted cytosines and 5-halocytosines. Journal of Heterocyclic Chemistry, Sep. 1, 1995, vol. 32, Nr:5, pp. 1513-1515.
Kulikowski et al. Methylation and tautomerism of 5-fluorocytosine nucleosides and their analogues. Journal Nucleic Acids Research, Jan. 1, 1978, vol. 4, pp. S7-S10.
Supplemental European Search Report for EP10807172 (PCT/US2010/044579), Dec. 7, 2012.
International Search Report for PCT/US2010/044592, Sep. 21, 2010.
International Search Report for PCT/US/2009/031683, Jan. 22, 2009.
Jaworski et al. Infrared spectra and tautomerism of 5-fluorocytosine, 5-bromocytosine and 5-iodocytosine. Matrix isolation and theoretical ab initio studies. Journal of Molecular Structure, Jan. 1, 1990, vol. 223, pp. 63-92.
Gabriella et al. Some 5-fluorosulfanilamidopyrimidines. Gazzetta Chimica Italiana, Jan. 1, 1963, vol. 93, Nr:10, pp. 1268-1278.
Zhang et al., Improved method for synthesis of 5-fluorocytosine (5-FC). CAPLUS Abstract 111:134074 (1989).
International Search Report for PCT/US2011/020351, Mar. 14, 2011.
Liang et al., A facile synthesis and herbicidal activities of novel fluorine-containing thiazolo[4,5-d] pyrimidin-7(6H)-ones. Journal of Fluorine Chemistry [online], Jul. 2007, vol. 128, Iss. 7, pp. 879-884.
Bera et al., Nucleosides with furanyl scaffolds. Tetrahedron, Jun. 10, 2002, vol. 58, Nr:24, pp. 4865-4871.
Duschinsky et al., Cytosine derivatives. CAPLUS Abstract 61:18527, 1964.
International Search Report for PCT/US2010/044588, Oct. 1, 2010.
International Search Report for PCT/US2012/050931, Oct. 9, 2012.
Waring, M J, Defining optimum lipophilicity and molecular weight ranges for drug candidates-Molecular weight dependent lower logD limits based on permeability. Bioorganic & Medical Chemistry Letters, May 15, 2009, vol. 19, Nr: 10, pp. 2844-2851.
International Search Report for PCT/US2010/060792, Apr. 22, 2011.
International Search Report for PCT/US2010/044576, Sep. 23, 2010.
Duschinsky et al., Nucleosides. XXXIII. N4-Acylated 5-Fluorocytosines and a Direct Synthesis of 5-Fluoro-2'-deoxycytidine. Journal of Medicinal Chemistry, Jul. 1, 1966, vol. 9, Nr:4, pp. 566-572.
C.G.Wermuth, The Practice of Medicinal Chemistry, Chapter 13, pp. 235-271, dated Aug. 15, 1998.

* cited by examiner

THIAZOLO[5,4-D] PYRIMIDINES AND THEIR USE AS AGROCHEMICALS

CROSS REFERENCE TO RELATED APPLICATIONS

This application claims the benefit of U.S. Provisional Patent Application Ser. No. 61/293,014 filed Jan. 7, 2010, which is expressly incorporated by reference herein.

FIELD OF THE INVENTION

The present disclosure relates to thiazolo[5,4-d]pyrimidines and their use as agrochemicals and animal health products.

BACKGROUND AND SUMMARY

The present disclosure provides novel organic compounds that may demonstrate activity as pesticides, meaning that they may control fungi, insects, mites, and/or animal parasites. The disclosure also provides novel pesticide methods and compositions utilizing the novel compounds.

More specifically, the invention provides new compounds of the formula (I-A):

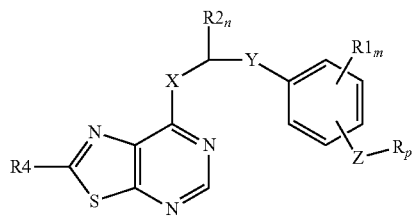

I-A wherein:

R is H, lower alkyl, lower haloalkyl, phenyl or a heterocycle;

Z is H, a C—C single bond, $CH_2$, NH, O, S, $CH_2O$ or $OCH_2$;

m is 4;

R1 are independently H, halo, lower alkyl, lower alkenyl, lower alkynyl, hydroxy, lower alkoxy, haloalkyl, haloalkoxy, $NO_2$, CN, lower alkanoyloxy, lower alkoxycarbonyl, formyl, lower alkanoyl, mercapto, lower alkylthio, and aldoximes and lower alkyloximes optionally substituted on oxygen by lower alkyl;

Y is a C—C single bond, $C(R5_n)O$ or $C(R5_n)$;

n is 2;

p is 0 or 1;

R2 are independently H or lower alkyl;

R5 are independently H or lower alkyl;

X is NR3 or O, where R3 is selected from H, lower alkyl, formyl, lower alkanoyl, lower alkoxycarbonyl, hydroxy, lower alkoxy, lower alkyl-$SO_q$, phenyl-$SO_q$ or substituted phenyl-$SO_q$ when q is an integer from 0 to 2; and R4 is H, alkyl, halo, haloalkyl, alkoxy or haloalkoxy.

The invention also provides new compounds of formula (I-B):

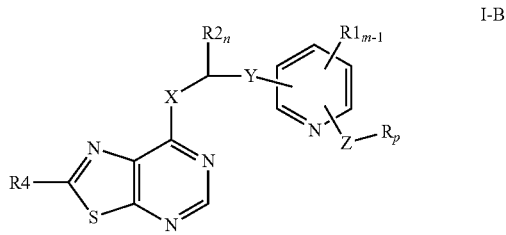

I-B wherein:

R is H, lower alkyl, lower haloalkyl, phenyl or a heterocycle;

Z is H, a C—C single bond, $CH_2$, NH, O, S, $CH_2O$ or $OCH_2$;

m is 4;

R1 are independently H, halo, lower alkyl, lower alkenyl, lower alkynyl, hydroxy, lower alkoxy, haloalkyl, haloalkoxy, $NO_2$, CN, lower alkanoyloxy, lower alkoxycarbonyl, formyl, lower alkanoyl, mercapto, lower alkylthio, and aldoximes and lower alkyloximes optionally substituted on oxygen by lower alkyl;

Y is a C—C single bond, $C(R5_n)O$ or $C(R5_n)$;

n is 2;

p is 0 or 1;

R2 are independently H or lower alkyl;

R5 are independently H or lower alkyl;

X is NR3 or O, where R3 is selected from H, formyl, lower alkyl, lower alkanoyl, lower alkoxycarbonyl, hydroxy, lower alkoxy, lower alkyl-$SO_q$, phenyl-$SO_q$ or substituted phenyl-$SO_q$ when q is an integer from 0 to 2; and R4 is H, alkyl, halo, haloalkyl, alkoxy or haloalkoxy.

The invention also provides new pesticide methods and compositions utilizing the compounds of formula (I-A) and (I-B).

The invention includes fungicidal, insecticidal, acaricidal, and parasiticidal compositions comprising an effective amount of a compound of the present invention in a mixture with an agriculturally acceptable or pharmaceutically acceptable adjuvant or carrier. The invention also includes methods of controlling a fungus, insect, mite, or parasite comprising applying an effective amount of a compound of the present invention to the fungus, insect or mite, soil, plant, root, foliage, seed, locus, or animal (for which purpose they may be administered orally, parenterally, percutaneously or topically) in which the infestation is to be prevented or cured.

DETAILED DESCRIPTION OF THE INVENTION

The compounds of the present invention are directed to compounds of formula (I-A)

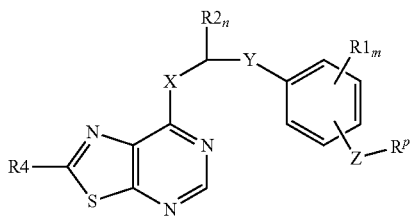

wherein p is 1 and R is an optionally substituted phenyl or heterocyclic system. More specifically, R may be selected from:

optionally substituted pyridinyl

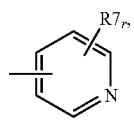

optionally substituted pyridinyl-N-oxide

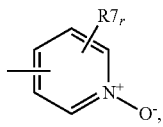

optionally substituted pyrazinyl

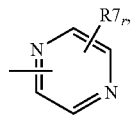

optionally substituted pyrimidinyl

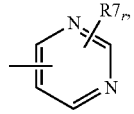

optionally substituted pyridazinyl

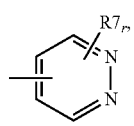

optionally substituted thiazolyl

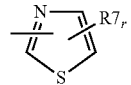

or optionally substituted heterocycles such as thienyl, furyl, oxazolyl, isoxazolyl, isothiazolyl, furazanyl, pyrrolyl, pyrazolyl or imidazolyl, where r is 4 in the case of pyridinyl, 3 in the case of pyrazinyl, pyrimidinyl, pyridazinyl, thienyl, furyl, and pyrrolyl, 2 in the case of thiazolyl, oxazolyl, isoxazolyl, isothiazolyl, pyrazolyl, imidazolyl, 1 in the case of furazanyl, and R7 are independently H, halo, lower alkyl, hydroxy, lower alkoxy, lower alkenyl, lower alkynyl, haloalkyl, haloalkoxy, $NO_2$, CN, lower alkanoyloxy, lower alkoxycarbonyl, formyl, lower alkanoyl and lower alkyl-$SO_q$ and q is an integer from 0 to 2, mercapto, lower alkylthio, and aldoximes and lower alkyloximes optionally substituted on oxygen by lower alkyl.

The compounds of the present invention also are directed to compounds of formula (I-B)

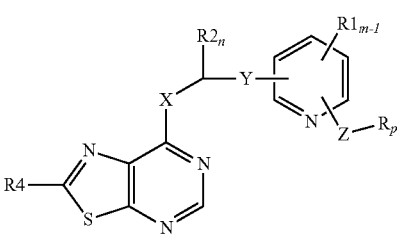

wherein p is 1 and R is lower alkyl, lower haloalkyl, an optionally substituted phenyl or heterocyclic system. More specifically, R may be selected from haloalkyl, or:

optionally substituted pyridinyl

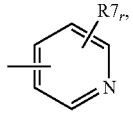

optionally substituted pyridinyl-N-oxide

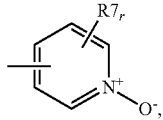

optionally substituted pyrazinyl

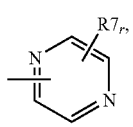

optionally substituted pyrimidinyl

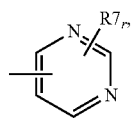

optionally substituted pyridazinyl

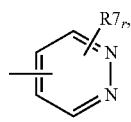

optionally substituted thiazolyl

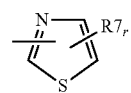

or optionally substituted heterocycles such as thienyl, furyl, oxazolyl, isoxazolyl, isothiazolyl, furazanyl, pyrrolyl, pyrazolyl or imidazolyl, where r is 4 in the case of pyridinyl, 3 in the case of pyrazinyl, pyrimidinyl, and pyridazinyl and 2 in the case of thiazolyl, and R7 are independently H, halo, lower alkyl, hydroxy, lower alkoxy, lower alkenyl, lower alkynyl, haloalkyl, haloalkoxy, $NO_2$, CN, lower alkanoyloxy, lower alkoxycarbonyl, formyl, lower alkanoyl and lower alkyl-$SO_q$ and q is an integer from 0 to 2, mercapto, lower alkylthio, and aldoximes and lower alkyloximes optionally substituted on oxygen by lower alkyl.

Throughout this document, all temperatures are given in degrees Celsius, and all percentages are weight percentages unless otherwise stated.

The terms "alkyl," "alkenyl" and "alkynyl," as well as derivative terms such as "alkoxy" and "alkylthio," as used herein, include within their scope straight chain, branched chain and cyclic moieties. The terms "alkenyl" and "alkynyl" are intended to include one or more unsaturated bonds.

The term "halo" refers to F, Cl, Br and I atoms.

The term "lower alkyl" refers to $C_1$ to $C_6$ straight hydrocarbon chains and $C_3$ to $C_6$ branched and cyclic hydrocarbon groups.

The terms "lower alkenyl" and "lower alkynyl" refer to $C_2$ to $C_6$ straight hydrocarbon chains and $C_3$ (or $C_4$ in the case of lower alkynyl) to $C_6$ branched hydrocarbon groups containing at least one unsaturated bond.

The terms "lower alkoxy" and "lower alkylthio" refer to O-lower alkyl and S-lower alkyl groups.

The term "haloalkyl" refers to lower alkyl groups substituted with one or more halo atoms.

The term "haloalkoxy" refers to lower alkoxy groups substituted with one or more halo atoms.

The term "substituted phenyl" refers to phenyl substituted with lower alkyl, lower alkenyl, lower alkynyl, lower alkoxy, lower alkylthio, halo, hydroxy, $NO_2$, haloalkyl, haloalkoxy, haloalkylthio, CN, phenyl, substituted phenyl, O-phenyl, O-substituted phenyl, $C_1$-$C_4$ alkanoyloxy, $C_1$-$C_4$ alkoxycarbonyl, lower alkanoyl, benzyloxy or lower alkyl-$SO_q$ and q is an integer from 0 to 2, mercapto, and aldoximes and lower alkyloximes optionally substituted on oxygen by lower alkyl.

The term oxime refers to any of a group of compounds containing a C=NOH group, formed by treating aldehydes or ketones with hydroxylamine. Oximes derived from aldehydes are called aldoximes; those from ketones are called ketoximes.

The terms pyridine- or pyridinyl-N-oxide refer to pyridine derivatives that may be prepared by heating the base [pyridine] with either hydrogen peroxide and acetic acid or preformed peracetic acid (Fieser and Fieser, *Reagents for Organic Synthesis*; John Wiley and Sons: New York, 1967; pp 464-465).

In the present invention, whenever multiple substituents are independently selected it is to be understood that they are selected so as to be sterically compatible with each other. Steric compatibility refers to the absence of steric hindrance as this term is defined in The Condensed Chemical Dictionary, 7th edition, Reinhold Publishing Co., N.Y. page 893 (1966), which definition is as follows:

steric hindrance. A characteristic of molecular structure in which the molecules have a spatial arrangement of their atoms such that a given reaction with another molecule is prevented or retarded in rate.

Steric compatibility is characterized by substituents whose physical bulk does not require confinement within volumes insufficient for the exercise of their normal behavior as discussed in D. J. Cram and G. Hammond, Organic Chemistry 2nd edition, McGraw-Hill Book Company, N.Y. page 215 (1964).

The compounds of this invention are made using well known chemical procedures. The required starting materials are commercially available or are readily synthesized using standard procedures.

Scheme I: Synthesis of compounds of formula (I-A) wherein X is O

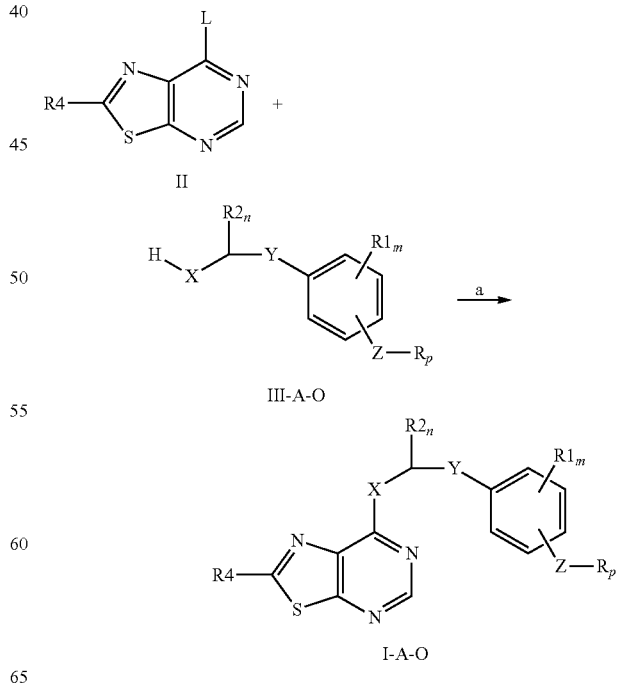

The compounds of formula (I-A) wherein X is O (I-A-O) may be made by condensing a compound of formula (II)

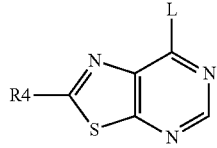

where R4 is as defined as for formula (I-A); and L is a leaving group, such as F, Cl, Br, I, NO$_2$, 1,2,3-triazol-1-yl, 1,2,4-triazol-1-yl, OSiMe$_3$, arylthio, alkylthio, alkylsulfonyl, arylsulfonyl, alkoxy, alkylsulfinyl or arylsulfinyl; with a compound of formula (III-A-O)

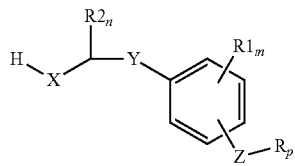

where R, Y, Z, R1, R2, m, n and p are as defined for formula (I-A) and X is O, as in step a of Scheme I. The reaction is preferably carried out in the presence of a base in a non-reactive solvent, such as dichloromethane, tetrahydrofuran (THF) or N,N-dimethylformamide (DMF), at a temperature in the range of 0° C. to reflux temperature.

The compounds of formula (I-A) wherein X is NR3, R3 is as defined for formula (I-A) and Z is oxygen (I-A-N), can be made by condensing a compound of formula (II)

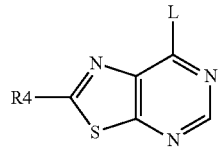

where R4 is as defined as for formula (I-A); and L is a leaving group, such as F, Cl, Br, I, NO$_2$, 1,2,3-triazol-1-yl, 1,2,4-triazol-1-yl, OSiMe$_3$, arylthio, alkylthio, alkylsulfonyl, arylsulfonyl, alkoxy, alkylsulfinyl or arylsulfinyl; with a compound of formula (III-A-N)

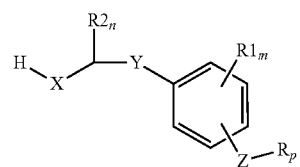

where R, Y, Z, R1, R2, m, n and p are as defined for formula (I-A) and X is NR3, R3 is as defined for formula (I-A), optionally as a salt (e.g., hydrochloride (HCl)), as in step e of Scheme II. The reaction is preferably carried out in the presence of a base, such as triethylamine, in a non-reactive solvent, such as dichloromethane, THF or DMF.

Scheme II: Synthesis of compounds of formula (I-A) wherein X is NR3

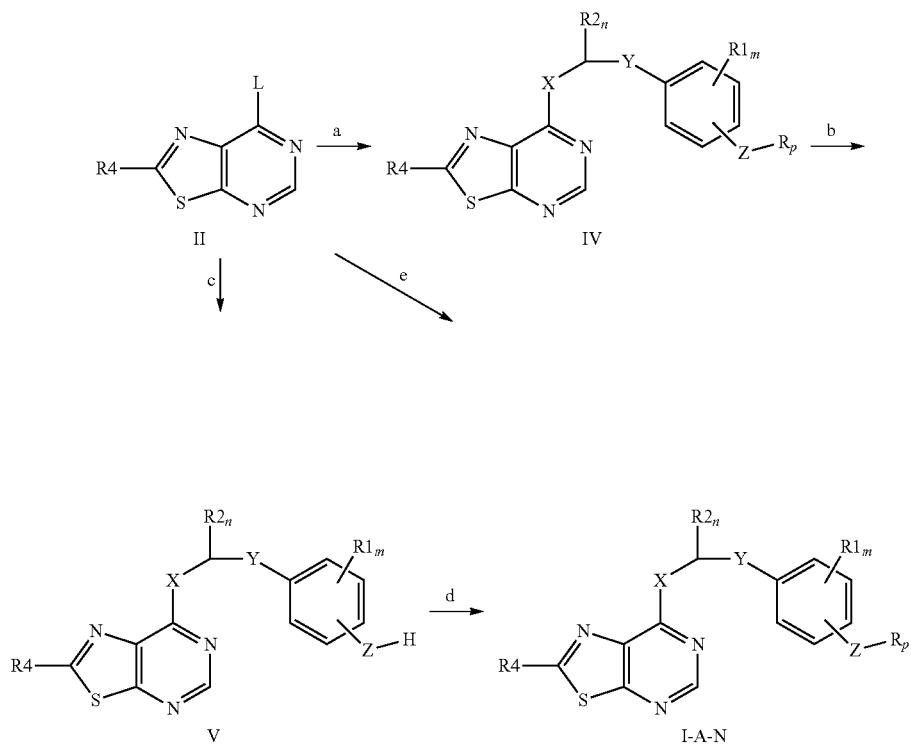

Compounds of formula (III-A-N) where R, R1, R2, Y, Z, m, n and p are as defined for formula (I-A) and X is NR3 and R3 is as defined for formula (I-A) may be prepared by well-known methods.

The compounds of formula (I-A) wherein X is NR3, R3 is as defined for formula (I-A) and Z is oxygen (I-A-N) where R is a heterocycle selected from the group consisting of pyridinyl, pyrazinyl, pyrimidinyl, pyridazinyl or thiazolyl wherein the heterocycle may be optionally substituted with one or more groups selected from halo, lower alkyl, lower alkenyl, lower alkynyl, lower alkoxy, haloalkyl, haloalkoxy, $NO_2$, CN, lower alkoxycarbonyl, lower alkanoyl, lower alkyl-$SO_q$, when q is an integer from 0 to 2, alkanoyloxy, formyl, mercapto, and aldoximes and lower alkyloximes optionally substituted on oxygen by lower alkyl;

alternatively are prepared by treatment of a compound of formula (V)

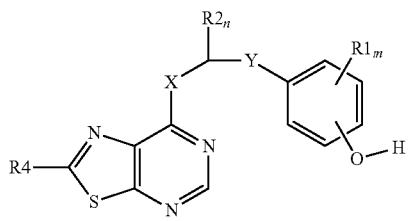

V wherein X is NR3; and R1, R2, R3, R4, Y, m and n are as defined for formula (I-A); with a heterocycle of formula L-Het where L is as defined for formula (II) and Het is a heterocycle selected from the group consisting of pyridinyl, pyrazinyl, pyrimidinyl, pyridazinyl or thiazolyl wherein the heterocycle may be optionally substituted with one or more groups selected from halo, lower alkyl, lower alkenyl, lower alkynyl, lower alkoxy, haloalkyl, haloalkoxy, $NO_2$, CN, lower alkoxycarbonyl lower alkanoyl and lower alkyl-$SO_q$, when q is an integer from 0 to 2, and aldoximes and lower alkyloximes optionally substituted on oxygen by lower alkyl, as in step d of Scheme II. The reaction is preferably carried out in the presence of a base, such as sodium hydride, in a nonreactive solvent, such as DMF.

The compounds of formula (I-A) wherein X is NR3, R3 is as defined for formula (I-A), Z is oxygen (I-A-N) and R is a phenyl, wherein the phenyl may be optionally substituted with one or more groups selected from halo, lower alkyl, lower alkenyl, lower alkynyl, lower alkoxy, haloalkyl, haloalkoxy, $NO_2$, CN, lower alkoxycarbonyl, lower alkanoyl, lower alkyl-$SO_q$, when q is an integer from 0 to 2, alkanoyloxy, formyl, mercapto, and aldoximes and lower alkyloximes optionally substituted on oxygen by lower alkyl;

alternatively are prepared by treatment of a compound of formula (V)

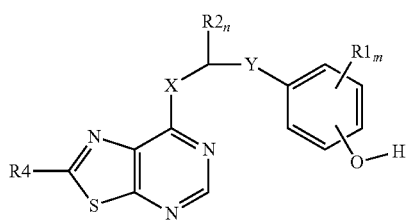

V wherein X is NR3; and R1, R2, R3, R4, Y, m and n are as defined for formula (I-A); with a compound of formula LG-Phe where LG is a leaving group such as fluoro, and Phe is a benzene optionally substituted with one or more groups selected from halo, lower alkyl, lower alkenyl, lower alkynyl, lower alkoxy, haloalkyl, haloalkoxy, $NO_2$, CN, lower alkoxycarbonyl, lower alkanoyl and lower alkyl-$SO_q$, when q is an integer from 0 to 2, and aldoximes and lower alkyloximes optionally substituted on oxygen by lower alkyl, as in step d of Scheme II. The reaction is preferably carried out in the presence of a base, such as sodium hydride, in a nonreactive solvent, such as DMF.

Certain compounds of formula (I-A-N) are prepared by modifications of other compounds of formula (I-A-N), as described in the Examples shown in the following section.

The compounds of formula (V) may be prepared by treatment of compounds of formula (IV)

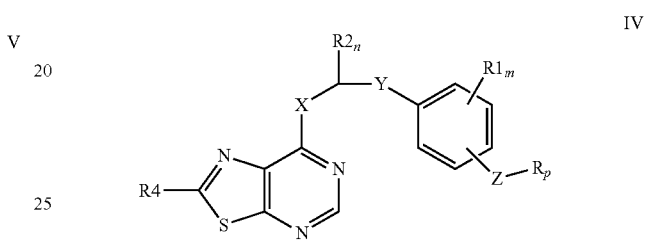

IV where X is NR3, Z is O and R1, R2, R3, R4, R, Y, m, n and p are as defined for formula (I-A), and R6 is lower alkyl; with a reagent such as boron tribromide ($BBr_3$) in a nonreactive organic solvent, such as dichloromethane, as in step b of Scheme II.

The compounds of formula (V) alternatively may be prepared by treatment of compounds of formula (II)

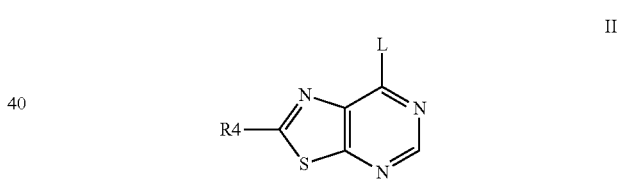

II where R4 is as defined as for formula (I-A); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl or arylsulfinyl; with a compound of formula (VI), optionally as a salt (e.g., HCl),

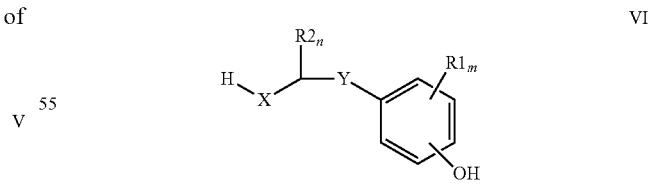

VI where X is NR3; and R1, R2, R3, Y, m and n are as defined for formula (I-A); optionally in the presence of a base, in a solvent such as acetonitrile, THF or DMF, as in step c of Scheme II.

Compounds of formula (IV) are prepared by the treatment of compounds of formula (II) wherein R4 is as described for compound (I-A); with a compound of formula (VII), optionally as a salt (e.g., HCl),

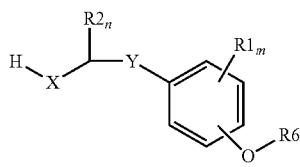

where X is NR3; and R1, R2, R3, Y, m and n are as defined for formula (I-A) and R6 is lower alkyl as in step e of Scheme II. The reaction is preferably carried out in the presence of a base, such as triethylamine, in a non-reactive solvent, such as dichloromethane, THF or DMF.

Compounds of formula (VII), where X is NR3; and R1, R2, R3, Y, m and n are as defined for formula (I-A) and R6 is lower alkyl, are commercially available or may be prepared by well-known methods. For example, compounds of formula (VII), where X is NR3; and R1, R2, m and n are as defined for formula (I-A), R6 is lower alkyl, R3 is H, and Y is $R5_n$, are prepared as their hydrochloride salts by treatment of appropriately substituted (4-alkoxyphenyl)-acetonitriles or of appropriately substituted 1-alkoxy-4-((E)-2-nitrovinyl)-benzenes with hydrogen in the presence of hydrochloric acid, a catalyst such as palladium on carbon, and an appropriate solvent such as ethyl alcohol.

Alternatively, compounds of formula (VII), where X is NR3; and R1, R2, m and n are as defined for formula (I-A), R6 is lower alkyl, R3 is H, Y is $R5_n$, are prepared by treatment of appropriately substituted (4-alkoxyphenyl)-acetonitriles with borane-dimethyl sulfide complex in an appropriate solvent such as THF at temperatures from 20° C. to reflux.

Alternatively, compounds of formula (VII), where X is NR3; and R1, R2, m and n are as defined for formula (I-A), R6 is alkyl or benzyl, R3 is H, and Y is $R5_n$, are prepared by treatment of the appropriately substituted 1-alkoxy-4-((E)-2-nitrovinyl)-benzenes with lithium aluminum hydride in an appropriate solvent such as THF.

The 1-alkoxy-4-((E)-2-nitrovinyl)-benzenes are prepared by treatment of the appropriately substituted benzaldehyde with nitromethane in the presence of ammonium acetate.

Scheme III: Synthesis of compounds of formula (I-B) wherein X is NR3

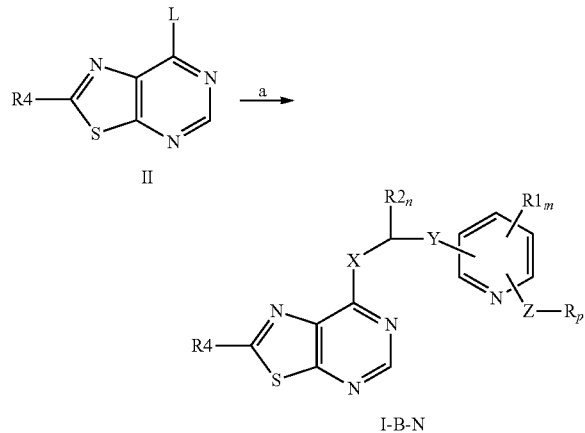

The compounds of formula (I-B) where X is NR3, and R3 is as defined for (1-B) and Z is oxygen (I-B-N) where R is haloalkyl, a substituted phenyl or a heterocycle selected from the group consisting of pyridinyl, pyrazinyl, pyrimidinyl, pyridazinyl or thiazolyl wherein the heterocycle may be optionally substituted with one or more groups selected from halo, lower alkyl, lower alkenyl, lower alkynyl, lower alkoxy, haloalkyl, haloalkoxy, $NO_2$, CN, lower alkoxycarbonyl, lower alkanoyl, lower alkyl-$SO_q$, when q is an integer from 0 to 2, alkanoyloxy, formyl, mercapto, and aldoximes and lower alkyloximes optionally substituted on oxygen by lower alkyl;

can be made by condensing a compound of formula (II)

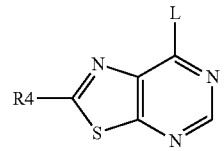

where R4 is as defined as for formula (I-B); and L is a leaving group, such as F, Cl, Br, I, $NO_2$, 1,2,3-triazol-1-yl, 1,2,4-triazol-1-yl, $OSiMe_3$, arylthio, alkylthio, alkylsulfonyl, arylsulfonyl, alkoxy, alkylsulfinyl or arylsulfinyl; with a compound of formula (III-B-N)

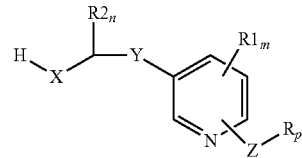

where X is NR3, and R, R1, R2, R3, Y, Z, m, n and p are as defined for formula (I-B), optionally as a salt (e.g., HCl), as in step a of Scheme III. The reaction is preferably carried out in the presence of a base, such as triethylamine, in a non-reactive solvent, such as dichloromethane, THF or DMF.

Amines of formula (III-B-N) where R, R1, R2, Y, Z, m, n and p are as defined for formula (I-B) and X is NH or N-lower alkyl may be prepared by well-known methods, as in Dreikorn, B. A.; Suhr, R. G.; Johnson, P. L. WO 9404527, 1994.

The compounds of the present invention may be pesticides that have fungitoxic activity against harmful fungi including, but not limited to, fungi that are pathogens of plants, animals, and humans. They are active against fungi of a number of classes including Oomycetes, Deuteromycetes (Fungi Imperfecti), Basidiomycetes, and Ascomycetes. More particularly, one embodiment of a method of the present invention provides for activity against phytopathogenic organisms including, but not limited to, *Pyricularia oryzae, Colletotrichum* species, *Erysiphe* species, *Puccinia* species, *Cochliobolus* species, *Alternaria* species, *Septoria* species, *Rhynchosporium secalis, Cercospora* and *Cercosporella* species, and *Pyrenophora* species. Additional diseases controlled include powdery mildews incited by *Sphaerotheca fulignea* (cucurbit powdery mildew) and *Uncinula necator* (grape powdery mildew), soybean rust incited by *Phakopsora pachyrhizi*, downy mildews such as cucumber downy mildew (*Pseudoperonospora cubensis*), grape downy mildew (*Plasmopara viticola*), apple scab incited by *Venturia inaequalis*, late blight incited by *Phytophthora infestans*, root rot caused by *Fusarium* species, gray mold caused by *Botrytis* species, damping off caused by *Pythium* species, and Maize smut (*Ustilago maydis*).

The compounds of the present invention may have insecticidal activity against harmful insects and mites including, but not limited to, insects that are pests or parasites of plants, animals, and humans.

In other embodiments, the invention disclosed in this document may be used to control pests of Phylum Nematoda, the Phylum Arthropoda, the Subphylum Chelicerata, the Class Arachnida, the Subphylum Myriapoda, the Class Symphyla, the Subphylum Hexapoda, the Class Insecta, and Coleoptera (beetles). A non-exhaustive list of these such pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculates* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document may be used to control Dermaptera (earwigs).

In another embodiment, the invention disclosed in this document may be used to control Dictyoptera (cockroaches). A non-exhaustive list of such pests includes, but is not limited to, *Blattella germanica* (German cockroach), *Blatta orientalis* (oriental cockroach), *Parcoblatta pennsylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus surinamensis* (Surinam cockroach), and *Supella longipalpa* (brownbanded cockroach).

In another embodiment, the invention disclosed in this document may be used to control Diptera (true flies). A non-exhaustive list of such pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document may be used to control Hemiptera (true bugs). A non-exhaustive list of such pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea,* and *Triatoma* spp. (bloodsucking conenose bugs/kissing bugs).

In another embodiment, the invention disclosed in this document may be used to control Homoptera (aphids, scales, whiteflies, leafhoppers). A non-exhaustive list of such pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani*

(foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicornis*, *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document may be used to control Hymenoptera (ants, wasps, and bees). A non-exhaustive list of such pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* spp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document may be used to control Isoptera (termites). A non-exhaustive list of such pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document may be used to control Lepidoptera (moths and butterflies). A non-exhaustive list of such pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leafperforator), *Caloptilia* spp. (leafminers), *Capua reticulana*, *Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella*, *Cossus cossus* (carpenter moth), *Crambus* spp. (sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia*

*inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth).

In another embodiment, the invention disclosed in this document may be used to control Mallophaga (chewing lice). A non-exhaustive list of such pests includes, but is not limited to, *Bovicola ovis* (sheep biting louse), *Menacanthus stramineus* (chicken body louse), and *Menopon gallinea* (common hen louse).

In another embodiment, the invention disclosed in this document may be used to control Orthoptera (grasshoppers, locusts, and crickets). A non-exhaustive list of such pests includes, but is not limited to, *Anabrus simplex* (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (katydids), *Schistocerca gregaria*, *Scudderia furcata* (forktailed bush katydid), and *Valanga nigricornis*.

In another embodiment, the invention disclosed in this document may be used to control Phthiraptera (sucking lice). A non-exhaustive list of such pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In another embodiment, the invention disclosed in this document may be used to control Siphonaptera (fleas). A non-exhaustive list of such pests includes, but is not limited to, *Ctenocephalides canis* (dog flea), *Ctenocephalides felis* (cat flea), and *Pulex irritans* (human flea).

In another embodiment, the invention disclosed in this document may be used to control Thysanoptera (thrips). A non-exhaustive list of such pests includes, but is not limited to, *Frankliniella fusca* (tobacco thrips), *Frankliniella occidentalis* (western flower thrips), *Frankliniella shultzei*, *Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document may be used to control Thysanura (bristletails). A non-exhaustive list of such pests includes, but is not limited to, *Lepisma* spp. (silverfish) and *Thermobia* spp. (firebrats).

In another embodiment, the invention disclosed in this document may be used to control Acarina (mites and ticks). A non-exhaustive list of such pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi*, *Aculus pelekassi*, *Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati*, *Oligonychus* spp., *Oligonychus coffee*, *Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae*, *Tetranychus* spp., *Tetranychus urticae* (two-spotted spider mite), and *Varroa destructor* (honey bee mite).

In another embodiment, the invention disclosed in this document may be used to control Nematoda (nematodes). A non-exhaustive list of such pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document may be used to control Symphyla (symphylans). A non-exhaustive list of such pests includes, but is not limited to, *Scutigerella immaculata*.

In another embodiment, the invention disclosed in this document may be used to control animal and human parasites. A non-exhaustive list of such pests includes, but is not limited to, arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g, bot fly, blow fly, screwworm, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongueworms.

Detailed information regarding pests may be found in the "Handbook of Pest Control—The Behavior, Life History, and Control of Household Pests" by Arnold Mallis, 9$^{th}$ Edition, copyright 2004 by GIE Media Inc, which is expressly incorporated by reference herein.

The present invention contemplates all vehicles by which the composition of the present invention can be formulated for delivery and use as a pesticide composition, including solutions, suspensions, emulsions, wettable powders and water dispersible granules, emulsifiable concentrates, granules, dusts, baits, and the like. Compositions suitable for administration to vertebrates or man include preparations suitable for oral, parenteral, percutaneous, e.g. pour-on, or topical administration.

Compositions for oral administration comprise one or more of the compounds of general formula I in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastrointestinal tract. Any of these may incorporate active ingredient contained within microcapsules or coated with acidlabile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, wax-smears, or pour-on preparations and devices (e.g. ear tags) attached externally to animals in such a way as to provide local or systemic arthropod control.

Typically, formulations for application to plants or soil are applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including and usually known as wettable powders or water dispersible granules; or liquids including and usually known as emulsifiable concentrates, aqueous suspensions or suspension concentrates, and aqueous emulsions or emulsions in water, or mixtures thereof such as suspension-emulsions. As will be readily appreciated, any material to which this composition can be added may be used, provided they yield the desired utility without significant interference with the desired activity of the pesticidally active ingredients as pesticidal agents and improved residual lifetime or decreased effective concentration is achieved.

Wettable powders, which may be compacted to form water dispersible granules, comprise an intimate mixture of one or more of the pesticidally active ingredients, an inert carrier and surfactants. The concentration of the pesticidally active ingredient in the wettable powder is usually from about 10 percent to about 90 percent by weight based on the total weight of the wettable powder, more preferably about 25 weight percent to about 75 weight percent. In the preparation of wettable powder formulations, the pesticidally active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled Emulsifiable concentrates of the pesticidally active ingredient comprise a convenient concentration, such as from about 10 weight percent to about 50 weight percent of the pesticidally active ingredient, in a suitable liquid, based on the total weight of the concentrate. The pesticidally active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents. The formulations can also contain other compatible additives, for example, plant growth regulators and other biologically active compounds used in agriculture.

Aqueous suspensions comprise suspensions of one or more water-insoluble pesticidally active ingredients dispersed in an aqueous vehicle at a concentration in the range from about 5 to about 50 weight percent, based on the total weight of the aqueous suspension. Suspensions are prepared by finely grinding one or more of the pesticidally active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compositions of the present invention can also be granular formulations, which are particularly useful for applications to the soil. Granular formulations usually contain from about 0.5 to about 10 weight percent, based on the total weight of the granular formulation of the pesticidally active ingredient(s), dispersed in an inert carrier which consists entirely or in large part of coarsely divided inert material such as attapulgite, bentonite, diatomite, clay or a similar inexpensive substance. Such formulations are usually prepared by dissolving the pesticidally active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the pesticidally active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the pesticidally active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain one or more other pesticidal compounds. Such additional pesticidal compounds may be fungicides, insecticides, nematicides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of the present invention, and the pesticidal compound in the combination can generally be present in a weight ratio of from 1:100 to 100:1.

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water soluble form e.g. (2,4-dichlorophenoxy)acetic acid dimethyl amine salt is a more water soluble form of (2,4-dichlorophenoxy)acetic acid, a well known herbicide.

The compounds disclosed in this invention can also form stable complexes with solvent molecules that remain intact after the non-complexed solvent molecules are removed from the compounds. These complexes are often referred to as "solvates."

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

The compounds of the present invention can also be combined with other agricultural fungicides to form fungicidal mixtures and synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with the other fungicide(s). Such other fungicides include but are not limited to 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mepanipyrim, mepronil, meptyl-dinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, Reynoutria sachalinensis extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis (dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamid, and any combinations thereof.

Additionally, the compounds of the present invention can be combined with other pesticides, including insecticides, nematicides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present invention are often applied in conjunction with one or more other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoatemethyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; oxadiazolone insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, fipronil, pyrafluprole, pyriprole, and vaniliprole; pyrethroid ester insecticides such as acrinathrin, allethrin, bioallethrin, barthrin, bifenthrin, bioethanomethrin, cyclethrin, cyclopro-thrin, cyfluthrin, beta-cyfluthrin, cyhalothrin, gamma-cyha-lothrin, lambda-cyhalothrin, cypermethrin, alpha-cyper-methrin, beta-cypermethrin, theta-cypermethrin, zeta-cypermethrin, cyphenothrin, deltamethrin, dimefluthrin, dimethrin, empenthrin, fenfluthrin, fenpirithrin, fenpropath-rin, fenvalerate, esfenvalerate, flucythrinate, fluvalinate, tau-fluvalinate, furethrin, imiprothrin, meperfluthrin, metof-luthrin, permethrin, biopermethrin, transpermethrin, phenothrin, prallethrin, profluthrin, pyresmethrin, res-methrin, bioresmethrin, cismethrin, tefluthrin, terallethrin, tetramethylfluthrin, tetramethrin, tralomethrin and trans-fluthrin; pyrethroid ether insecticides such as etofenprox, flufenprox, halfenprox, protrifenbute and silafluofen; pyrim-idinamine insecticides such as flufenerim and pyrimidifen; pyrrole insecticides such as chlorfenapyr; tetramic acid insec-ticides such as spirotetramat; tetronic acid insecticides such as spiromesifen; thiourea insecticides such as diafenthiuron; urea insecticides such as flucofuron and sulcofuron; and unclassified insecticides such as closantel, copper naphthen-ate, EXD, fenazaflor, fenoxacrim, hydramethylnon, isopro-thiolane, malonoben, metaflumizone, nifluridide, plifenate, pyridaben, pyridalyl, pyrifluquinazon, rafoxanide, sulfoxa-flor, triarathene, and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergis-tic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not lim-ited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; aryla-lanine herbicides such as benzoylprop, flamprop and flam-prop-M; chloroacetanilide herbicides such as acetochlor, alachlor, butachlor, butenachlor, delachlor, diethatyl, dimeth-achlor, metazachlor, metolachlor, S-metolachlor, preti-lachlor, propachlor, propisochlor, prynachlor, terbuchlor, the-nylchlor and xylachlor; sulfonanilide herbicides such as benzofluor, perfluidone, pyrimisulfan and profluazol; sul-fonamide herbicides such as asulam, carbasulam, fenasulam and oryzalin; thioamide herbicides such as chlorthiamid; antibiotic herbicides such as bilanafos; benzoic acid herbi-cides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlo-rthal; picolinic acid herbicides such as aminopyralid, clopy-ralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenate; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as 4-amino-3-chloro-6-(4-chloro-2-fluoro-3-methoxyphenyl)picolinic acid, aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

The compounds of the present invention may have broad ranges of efficacy as fungicides and insecticides. The exact amount of the active material to be applied is dependent not only on the specific active material being applied, but also on the particular action desired, the pathogen or pest to be controlled, and the stage of growth thereof, as well as the part of the plant, animal or other medium to be contacted with the compound. Thus, all the compounds, and formulations containing the same, may not be equally effective at similar concentrations or against the same pathogen and pest species.

The compounds are effective in use with plants in a phytologically acceptable amount. The term "phytologically acceptable amount" refers to an amount of a compound that kills or inhibits the pest or plant disease for which control is desired, but is not significantly toxic to the plant. This amount will generally be from about 0.1 to about 1000 parts per million (ppm), with 1 to 500 ppm being preferred.

The exact concentration of compound required varies with the pest or disease to be controlled, the type of formulation employed, the method of application, the particular plant or animal species, climate conditions, and the like. For fungicides, dilution and rate of application will depend upon the type of equipment employed, the method and frequency of application desired and diseases to be controlled, but the effective amount is usually from about 0.01 kilogram (kg) to about 20 kg of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed-applied fungicide, the amount of toxicant coated on the seed is usually at a dosage rate of about 0.1 to about 250 grams (g) and preferably from about 1 to about 60 g per 100 kg of seed. As a soil fungicide, the chemical can be incorporated in the soil or applied to the surface of the soil or a rice nursery box usually at a rate of about 0.1 to about 5 kg per hectare.

The actual amount of insecticide or miticide to be applied to loci of pests is generally not critical and can readily be determined by those skilled in the art. In general, concentrations from about 0.01 g of pesticide per hectare to about 5000 g of pesticide per hectare are expected to provide good control.

The locus to which a pesticide is applied can be any locus inhabited by any pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduced more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention may be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document may be suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document may also be employed advantageously in livestock keeping, for example, cattle, sheep, pigs, chickens, and geese. Suitable formulations may be administered orally to the animals with the drinking water or feed. The dosages and formulations that are suitable depend on the species.

In particular, the compounds of the present invention may effectively control a variety of undesirable insects and fungi that infect useful plant crops. Activity may be demonstrated against a variety of fungi, including those causing the following plant diseases: Anthracnose of Cucumber (*Colletotrichum lagenarium*); Powdery Mildew of Cucumber (*Erysiphe* spp.); Glume Blotch of Wheat (*Septoria nodorum*); Downy Mildew of Cucumber (*Pseudoperonospora cubensis*); Rice Blast (*Magnaporthe grisea*); Brown Rust of Wheat (*Puccinia recondita tritici*); Septoria Blotch of Wheat (*Septoria tritici*); Apple scab (*Venturia inaequalis*); Downy mildew of grape (*Plasmopara viticola*); Powdery mildew of wheat (*Erysiphe graminis*); Powdery mildew of grape (*Uncinula necator*); Late blight (*Phytophthora infestans*); Early blight (*Alternaria solani*); Spot blotch of cereals (*Cochliobolus sativus*); Rice sheath blight (*Rhizoctonia solani*), and Maize smut (*Ustilago maydis*).

Activity may be demonstrated by these compounds on a variety of insects, including Beet Armyworm (*Spodoptera exigua*), Mosquito (*Aedes aegypti*), Fruit Fly (*Drosophila melanogaster*), Green peach aphid (*Myzus persicae*), Cotton aphid (*Aphis gossypii*), and Bollworm/corn earworm (*Helicoverpa zea*).

It will be understood by those in the art that the efficacy of the compound on the foregoing fungi and insects establishes the general utility of the compounds as fungicides, insecticides, acaricides, and parasiticides.

Representative Experimental Procedures
Chromatography Definitions
Prep RP-HPLC (preparative reverse-phase high-performance liquid chromatography):
20 mm×250 mm S5 μm 120 Å YMC-AQ, or 50 mm×250 mm S10 μm 120 Å YMC-AQ column, using 0.1% v/v phosphoric acid ($H_3PO_4$) mixtures with acetonitrile/water ($CH_3CN/H_2O$) as eluent;
HPLC (high performance liquid chromatography): $CH_3CN/H_2O$ solvent system over $C_8$-$C_{18}$ on silica gel support
TLC (thin layer chromatography): silica gel ($SiO_2$)/glass plates, eluted with hexane, diethyl ether ($Et_2O$), dichloromethane ($CH_2Cl_2$), ethyl acetate (EtOAc), methyl alcohol (MeOH), or any useful mixture of these;
GC (gas chromatography);
GC-MS (gas chromatography-mass spectrometry)
LC-MS (liquid chromatography-mass spectrometry)
NMR: s=singlet, br=broad, m=multiplet, d=doublet, dd=doublet of doublets, ddd=doublet of doublets of doublets, t=triplet, q=quartet; field strength 300 MHz (unless otherwise noted).

Example 1

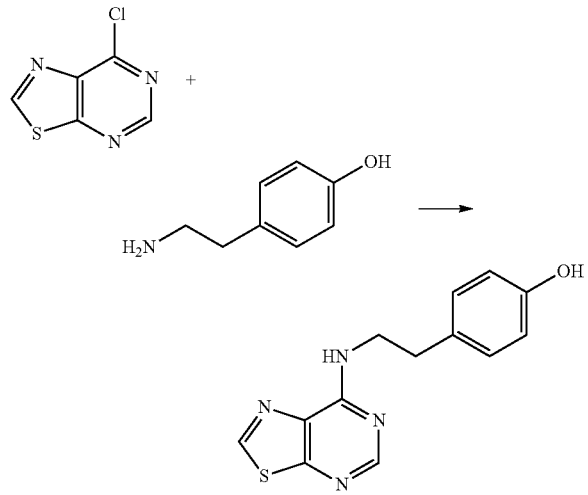

4-[2-(Thiazolo[5,4-d]pyrimidin-7-ylamino)-ethyl]-phenol. 7-Chlorothiazolo[5,4-d]pyrimidine (2.71 grams (g), 15.7 millimoles (mmol)) and tyramine (2.16 g, 15.7 mmol) were dissolved with magnetic stirring in N,N-dimethylformamide (DMF; 20 milliliters (mL)) in a 100 mL round bottom flask equipped with a reflux condenser and a dry nitrogen line at 25° C. To the solution was added potassium carbonate ($K_2CO_3$; 6.0 g, 43.4 mmol), and the mixture was heated at 100° C., then cooled to 25° C., and stirred overnight. The reaction was diluted with water ($H_2O$; 150 mL), and then treated with 2 N hydrochloric acid (HCl) to adjust the pH to 6. The aqueous layer was washed repeatedly with EtOAc, and the pooled organic fractions were filtered and concentrated in vacuo to provide 4-[2-(thiazolo[5,4-d]pyrimidin-7-ylamino)-ethyl]-phenol (Compound 3; 1.0 g) as an amber powder: mp 161-168° C.; $^1$H NMR (DMSO-$d_6$) δ 9.24 (s, 1H), 9.18 (s, 1H), 8.42 (s, 1H), 8.29 (br s, 1H), 7.04 (d, J=8.0 Hz, 2H), 6.67 (d, J=8.3 Hz, 2H), 3.65 (m, 2H), 2.81 (m, 2H); ESIMS m/z 273.1 ([M+H]$^+$).

Prepared in the same way:
Compound 1, [1-(4-Methoxyphenyl)-ethyl]-thiazolo[5,4-d]pyrimidin-7-yl-amine.

Example 2

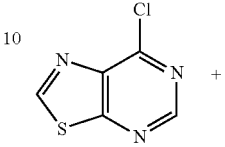

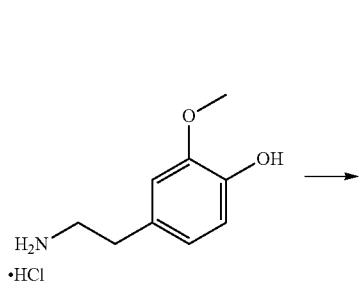

2-Methoxy-4-[2-(thiazolo[5,4-d]pyrimidin-7-ylamino)-ethyl]-phenol. 7-Chlorothiazolo[5,4-d]pyrimidine (350 milligrams (mg), 2 mmol) and 4-(2-aminoethyl)-2-methoxyphenol hydrochloride (410 mg, 2 mmol) were dissolved with magnetic stirring in warm DMF (10 mL) in a 100 mL round bottom flask equipped with a reflux condenser and a dry nitrogen line. The solution was cooled to room temperature and then treated with sodium hydride (NaH, 60% dispersion in oil; 250 mg, 6.25 mmol). After stirring for 1 hour (h), the mixture was diluted with $H_2O$ (120 mL) and neutralized with 2 N HCl. After stirring for another hour, the suspension was filtered. The filtrate was washed with an equivolume of 1:1 $Et_2O$/EtOAc. The organic fraction was filtered and concentrated in vacuo to afford 310 mg of a yellow gum. This material was dissolved in a minimum volume of $CH_2Cl_2$, and then diluted with hexane while heating at reflux to boil off the $CH_2Cl_2$. The cloudy supernatant was decanted away from the yellow film which had precipitated. Upon cooling the supernatant to room temperature, a solid formed. This supernatant was poured off to afford 2-methoxy-4-[2-(thiazolo[5,4-d]pyrimidin-7-ylamino)-ethyl]-phenol (Compound 12; 70 mg) as beige crystals: mp 151-154° C.; $^1$H NMR (DMSO-$d_6$) δ 9.18 (s, 1H), 8.66 (s, 1H), 8.40 (s, 1H), 8.18 (t, J=5.7 Hz, 1H), 6.78

(d, J=1.4 Hz, 1H), 6.68 (d, J=8.0 Hz, 1H), 6.63 (dd, J=8.0, 1.7 Hz, 1H), 3.77-3.67 (m, 5H), 2.84 (t, J=7.5 Hz, 2H); ESIMS m/z 303.1 ([M+H]+).

Example 3

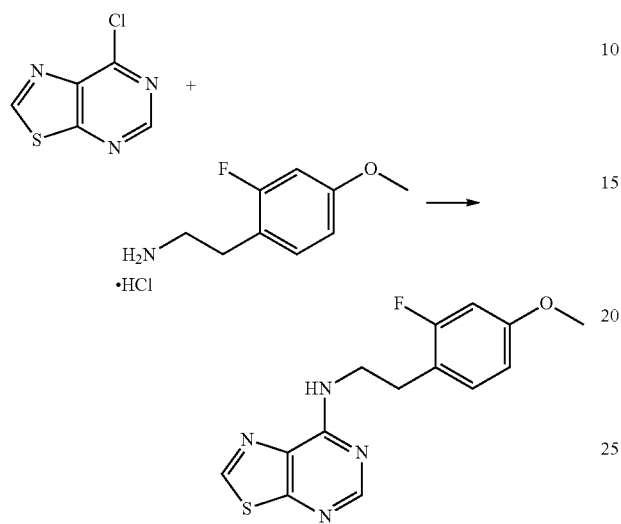

[2-(2-Fluoro-4-methoxyphenyl)-ethyl]-thiazolo[5,4-d]pyrimidin-7-ylamine 7-Chlorothiazolo[5,4-d]pyrimidine (564 mg, 3.3 mmol) was dissolved with magnetic stirring in DMF (10 mL) in a 25 mL round bottom flask equipped with a dry nitrogen line at 25° C. To the solution was added 2-(2-fluoro-4-methoxyphenyl)-ethylamine hydrochloride (700 mg, 3.4 mmol) and triethylamine (Et₃N, 1.19 mL, 8.5 mmol). After stirring overnight, the reaction was diluted with saturated (satd) aqueous (aq) ammonium chloride (NH₄Cl; 10 mL) and concentrated in vacuo. The residue was partitioned between H₂O (10 mL) and EtOAc (3×10 mL). The pooled organic fractions were diluted with pentane (15 mL), washed with H₂O (10 mL) and brine (10 mL). After drying (sodium sulfate; Na₂SO₄), the solution was filtered through a SiO₂/cotton plug, and concentrated in vacuo to provide 0.38 g. The aqueous fractions were washed with additional EtOAc, dried (Na₂SO₄) and filtered through a SiO₂/cotton plug, and concentrated in vacuo to provide an additional 0.23 g of crude product. The two fractions were combined and purified by flash column chromatography (SiO₂, 0-100% EtOAc/hexane). The appropriate fractions were pooled to afford [2-(2-fluoro-4-methoxyphenyl)-ethyl]-thiazolo[5,4-d]pyrimidin-7-ylamine (Compound 55; 230 mg) as a gold solid: mp 136-139° C.; ¹H NMR (DMSO-d₆) δ 9.21 (s, 1H), 8.39 (s, 1H), 8.32 (br m, 1H), 7.19 (t, J=8.7 Hz, 1H), 6.77-6.67 (m, 2H), 3.74-3.67 (m, 5H), 2.89 (t, J=7.4 Hz, 3H); ESIMS m/z 305.5 ([M+H]+).

Prepared in the same way:

Compound 10, [2-(4-methoxy-2,5-dimethylphenyl)-ethyl]-thiazolo[5,4-d]pyrimidin-7-ylamine.

Compound 15, 4-[2-(thiazolo[5,4-d]pyrimidin-7-ylamino)-propyl]-phenol.

Compound 19, [2-(4-methoxy-3-methylphenyl)-ethyl]-thiazolo[5,4-d]pyrimidin-7-ylamine.

Compound 21, [2-(3-bromo-4-methoxyphenyl)-ethyl]-thiazolo[5,4-d]pyrimidin-7-ylamine.

Compound 28, [2-(4-methoxy-2,3-dimethylphenyl)-ethyl]-thiazolo[5,4-d]pyrimidin-7-ylamine.

Compound 56, [2-(4-methoxy-2-methylphenyl)-ethyl]-thiazolo[5,4-d]pyrimidin-7-ylamine.

Preparation 1

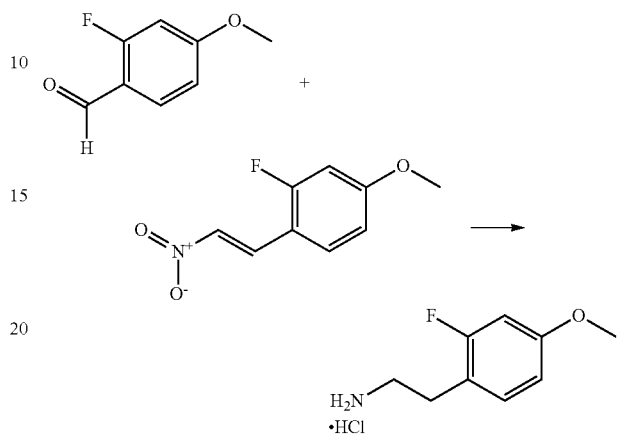

Step 1. 2-Fluoro-4-methoxy-1-((E)-2-nitrovinyl)benzene. A solution of 2-fluoro-4-methoxybenzaldehyde (5.0 g, 33 mmol) and ammonium acetate (NH₄OAc; 1.0 g, 13 mmol) in nitromethane (40 mL) was heated on a steam bath for 2.5 h. The reaction mixture was concentrated under reduced pressure, and the sticky residue was partitioned between CH₂Cl₂ and H₂O. The organic layer was washed with half-saturated brine, dried (magnesium sulfate; MgSO₄), filtered, and concentrated. The residue was triturated in hexane and the solid was filtered and washed with hexane and dried to give 2-fluoro-4-methoxy-1-(E)-2-nitrovinyl)benzene (5.57 g) as an orange solid: mp 80-82° C. This material was used in the next step without additional purification. ¹H NMR (CDCl₃) δ 8.02 (d, J=13.5 Hz, 1H), 7.66 (d, J=13.5 Hz, 1H), 7.43 (m, 1H), 6.80-6.68 (m, 2H), 3.87 (s, 3H); EIMS m/z 197 ([M]+).

Step 2. 2-(2-Fluoro-4-methoxyphenyl)ethylamine hydrochloride. Under a nitrogen atmosphere, 2-fluoro-4-methoxy-1-((E)-2-nitrovinyl)benzene (26.5 g, 134.5 mmol) was added in portions to a suspension of lithium aluminum hydride (LiAlH₄; 16 g, 195 mmol) in THF (1 liter (L)) at 0° C. The mixture then was heated at reflux, and after 3.5 h, the reaction mixture was cooled to 0° C. and quenched carefully with H₂O (34.6 mL) and 10% aq sodium hydroxide (NaOH; 28 mL). After removal of green precipitates by suction filtration, the filtrate was dried (MgSO₄), filtered and evaporated under reduced pressure. The oily residue was dissolved in EtOAc (150 mL) and then concentrated (conc.) HCl was added to adjust the pH to approximately 1. Et₂O (1 L) was added with stirring, the solid was collected by suction filtration and washed with a small amount of acetone, and then was dried under vacuum to give 12.3 g of 2-(2-fluoro-4-methoxyphenyl)ethylamine hydrochloride as a white solid, mp 162-165° C. The filtrate was concentrated under reduced pressure, and the residue was dried azeotropically by suspending in toluene and concentrating in vacuo. The residue was dissolved in methyl alcohol (MeOH), and the solution was diluted with EtOAc to precipitate additional product. The second crop was collected by suction filtration and washed with EtOAc, affording another 7.3 g of product. The total yield was 19.6 g (72%). ¹H NMR (CDCl₃) δ 8.29 (br, 3H), 7.24 (t, J=8.7 Hz, 1H), 6.84-6.73 (m, 2H), 3.74 (s, 3H), 2.99-2.83 (m, 4H); ESIMS m/z 169.9 ([M]$^+$–HCl).

Example 4

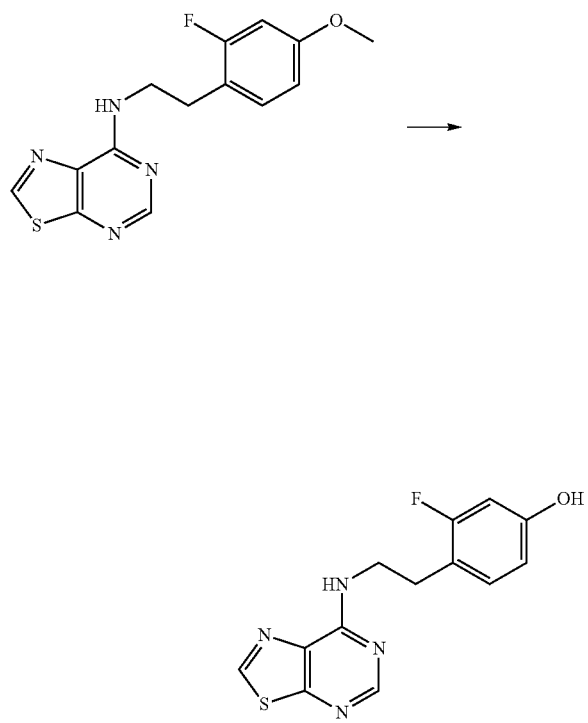

3-Fluoro-4-[2-(thiazolo[5,4-d]pyrimidin-7-ylamino)-ethyl]-phenol. [2-(2-Fluoro-4-methoxy-phenyl)-ethyl]-thiazolo[5,4-d]pyrimidin-7-ylamine (204 mg, 0.67 mmol) was dissolved in CH$_2$Cl$_2$ (3.4 mL) in a 25 mL round bottom flask equipped with a magnetic stir bar, a septum and a dry nitrogen line. After cooling to 0° C., the solution was treated with 1.0 M boron tribromide (BBr$_3$) solution in CH$_2$Cl$_2$ (3.4 mL), and the reaction mixture became brown. After stirring 3 h at 0° C., the mixture was treated with satd aq sodium bicarbonate (NaHCO$_3$; 10 mL) and stirred at 0° C. for another hour. The precipitate was collected by suction filtration, washed with cold H$_2$O (2×5 mL), and air dried on the filter to provide 3-fluoro-4-[2-(thiazolo[5,4-d]pyrimidin-7-ylamino)-ethyl] phenol (Compound 58; 127 mg) as a beige powder: mp 193° C.; $^1$H NMR (DMSO-d$_6$) δ 9.64 (br s, 1H), 9.24 (s, 1H), 8.42 (br m, 2H), 7.07 (t, J=8.8 Hz, 1H), 6.53-6.49 (m, 2H), 3.71-3.66 (m, 2H), 2.85 (t, J=7.3 Hz, 2H); ESIMS: m/z 291.2 ([M+H]$^+$).

Prepared in the same way:

Compound 11, 2,5-dimethyl-4-[2-(thiazolo[5,4-d]pyrimidin-7-ylamino)-ethyl]-phenol.

Compound 20, 2-methyl-4-[2-(thiazolo[5,4-d]pyrimidin-7-ylamino)-ethyl]-phenol.

Compound 25, 2-bromo-4-[2-(thiazolo[5,4-d]pyrimidin-7-ylamino)-ethyl]-phenol.

Compound 26, 2,3-dimethyl-4-[2-(thiazolo[5,4-d]pyrimidin-7-ylamino)-ethyl]-phenol.

Compound 39, 2-fluoro-4-[2-(thiazolo[5,4-d]pyrimidin-7-ylamino)-ethyl]-phenol.

Compound 57, 3-methyl-4-[2-(thiazolo[5,4-d]pyrimidin-7-ylamino)-ethyl]-phenol.

Example 5

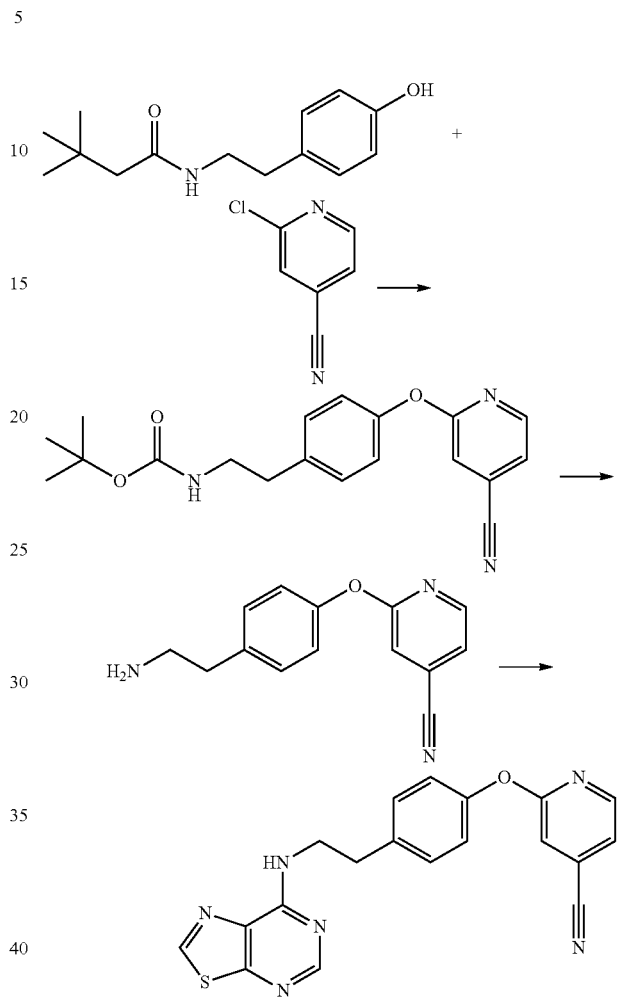

2-{4-[2-(Thiazolo[5,4-d]pyrimidin-7-ylamino)-ethyl]-phenoxy}-isonicotinonitrile. 7-Chlorothiazolo[5,4-d]pyrimidine (0.26 g, 1.5 mmol), 2-[4-(2-aminoethyl)-phenoxy]-isonicotinonitrile (0.36 g, 1.5 mmol) and Et$_3$N (231 mg, 2.3 mmol) were dissolved with magnetic stirring in DMF (10 mL) in a 25 mL round bottom flask equipped with a dry nitrogen line at 25° C. After stirring overnight, the reaction was diluted with H$_2$O (100 mL) and neutralized with 2 N HCl. The mixture was partitioned into a 1:1 solution of EtOAc/Et$_2$O (3×50 mL). The pooled organic fractions were filtered and concentrated in vacuo to afford a yellow gum, 0.54 g. The gum was dissolved in a small volume of EtOAc and passed through a short SiO$_2$ column with EtOAc/Et$_2$O eluent. The appropriate fractions were pooled and concentrated in vacuo to afford 2-{4-[2-(thiazolo[5,4-d]pyrimidin-7-ylamino)-ethyl]-phenoxy}-isonicotinonitrile (Compound 2; 230 mg) as a white solid: mp 145-148° C.; $^1$H NMR (400 MHz, CDCl$_3$) δ 8.77 (s, 1H), 8.55 (s, 1H), 8.33 (dd, J=5.1, 0.7 Hz, 1H), 7.39-7.29 (m, 2H), 7.20 (dd, J=5.1, 1.3 Hz, 1H), 7.17-7.13 (m, 1H), 7.13-7.06 (m, 2H), 6.27 (s, 1H), 3.95 (dd, J=12.6, 6.2 Hz, 2H), 3.05 (t, J=7.1 Hz, 2H); ESIMS m/z 375.2 ([M+H]$^+$).

Prepared in the same way:

Compound 40, thiazolo[5,4-d]pyrimidin-7-yl-{2-[4-(2-trifluoromethylpyridin-4-yloxy)-phenyl]-ethyl}-amine.

Compound 44, (2-dibenzofuran-2-ylethyl)-thiazolo[5,4-d]pyrimidin-7-yl-amine.

Preparation 2

{2-[4-(4-Cyanopyridin-2-yloxy)-phenyl]-ethyl}-carbamic acid tert-butyl ester. [2-(4-Hydroxyphenyl)-ethyl]-carbamic acid tert-butyl ester (5.31 g, 22.4 mmol) and 2-chloroisonicotinonitrile (3.27 g, 22.4 mmol) were dissolved with magnetic stirring in dimethyl sulfoxide (DMSO; 50 mL) in a 250 mL round bottom flask equipped with a reflux condenser and a dry nitrogen line at 25° C. To the solution was added $K_2CO_3$ (6.0 g, 43.5 mmol), and the reaction mixture was slowly heated to 135-140° C. over 1 h. The reaction was filtered, concentrated in vacuo, and diluted with $H_2O$ (500 mL). The precipitate which formed was collected by suction filtration, dissolved in $CH_2Cl_2$ and treated with decolorizing carbon. The mixture was filtered and concentrated in vacuo to afford {2-[4-(4-cyanopyridin-2-yloxy)-phenyl]-ethyl}-carbamic acid tert-butyl ester (5.57 g) as a beige solid: mp 92-96° C.; $^1$H-NMR (CDCl$_3$) δ 8.32 (d, J=5.3 Hz, 1H), 7.26 (m, 2H), 7.20 (dd, J=5.1, 0.8 Hz, 1H), 7.16 (m, 1H), 7.10-7.04 (m, 3H), 3.40 (br m, 2H), 2.83 (m, 2H), 1.45 (s, 9H); ESIMS m/z 284.2 ([M−C$_4$H$_8$+H]$^+$). This material was used without further purification in the next step.

Prepared in the same way:

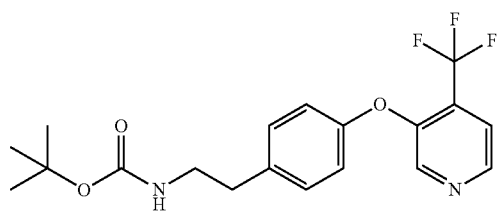 [SMILES: CC(C)(C)OC(=O)NCCc1ccc(Oc2cnccc2C(F)(F)F)cc1]

{2-[4-(4-Trifluoromethylpyridin-3-yloxy)-phenyl]-ethyl}-carbamic acid tert-butyl ester as a colorless oil, from 3-fluoro-4-trifluoromethylpyridine: ESIMS m/z 382 ([M]$^+$).

2-[4-(2-Aminoethyl)-phenoxy]-isonicotinonitrile: {2-[4-(4-Cyanopyridin-2-yloxy)-phenyl]-ethyl}-carbamic acid tert-butyl ester (5.57 g, 8.2 mmol) was dissolved with magnetic stirring in $CH_2Cl_2$ (100 mL) in a 250 mL round bottom flask equipped with a dry nitrogen line at 25° C. To this solution was added trifluoroacetic acid (10 mL), and the reaction mixture was kept at 25° C. for 3 h. The solution was concentrated in vacuo. The residue was taken up in $H_2O$ (50 mL) and EtOAc (75 mL) and treated with conc. ammonium hydroxide (NH$_4$OH) to adjust the pH to 9-10. The layers were separated, and the aqueous fraction was extracted twice with EtOAc. The pooled organic fractions were filtered and concentrated in vacuo to afford 2-[4-(2-aminoethyl)-phenoxy]-isonicotinonitrile (3.52 g, 89%) as a beige waxy solid: $^1$H NMR (400 MHz, CDCl$_3$) δ 8.32 (d, J=5.1 Hz, 1H), 7.27 (m, 2H), 7.19 (d, J=5.1 Hz, 1H), 7.15 (s, 1H), 7.07 (d, J=8.4 Hz, 2H), 3.00 (t, J=6.9 Hz, 2H), 2.78 (t, J=6.9 Hz, 2H), 1.63 (s, 2H); ESIMS m/z 240.1 ([M+H]$^+$).

Prepared in the same way:

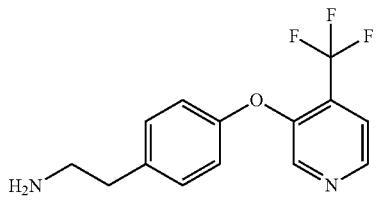 [SMILES: NCCc1ccc(Oc2cnccc2C(F)(F)F)cc1]

2-[4-(4-Trifluoromethylpyridin-3-yloxy)-phenyl]-ethylamine as a tan oil, from {2-[4-(4-trifluoromethylpyridin-3-yloxy)-phenyl]-ethyl}-carbamic acid tert-butyl ester: GC-MS m/z 282.

Preparation 3

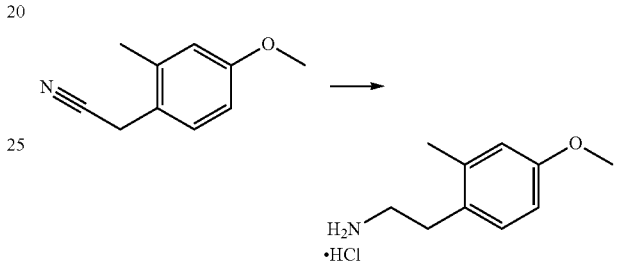

2-(4-Methoxy-2-methylphenyl)-ethylamine hydrochloride. 4-Methoxy-2-methylphenylacetonitrile (3.0 g, 18.6 mmol) was dissolved in absolute denatured ethyl alcohol (65 mL). To the solution was added conc. HCl (2.4 mL) and 10% Pd/C (300 mg). The suspension was deaerated in a 500 mL Parr hydrogenation bottle, then pressurized with 55 pounds per square inch (psi) hydrogen (H$_2$) and shaken. After 20 h, the reaction was recharged with H$_2$ and 10% Pd/C. After a total of 96 h, the reaction mixture was filtered through Celite and the filtrate was concentrated in vacuo. The off-white solid residue was recrystallized from isopropyl alcohol and collected by suction filtration to afford 2-(4-methoxy-2-methylphenyl)-ethylamine hydrochloride (1.86 g, 50%) as a white solid, mp 220-222° C. (gradual softening and discoloration from 104-220° C.). The filtrate was concentrated in vacuo and the residue was washed with EtOAc and filtered, providing an additional 1.34 g for a total yield of 3.2 g (85%): $^1$H NMR (DMSO-d$_6$) 8.25 (br s, 3H), 7.09 (d, 1H), 6.75 (m, 2H), 3.71 (s, 3H), 2.87 (m, 4H), 2.27 (s, 3H); GC-MS m/z 165 ([M−Cl]$^+$).

Prepared in the same way:

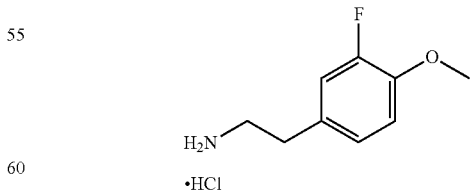

2-(3-Fluoro-4-methoxyphenyl)-ethylamine hydrochloride, from 4-methoxy-3-fluorophenylacetonitrile, as a tan powder: mp 220-221° C.; $^1$H NMR (400 MHz, DMSO-d$_6$) δ 8.25 (s, 3H), 7.02-7.18 (m, 3H), 3.82 (s, 3H), 2.95-3.05 (m, 2H), 2.85-2.90 (m, 2H); GC-MS m/z 169.0 ([M−Cl]$^+$).

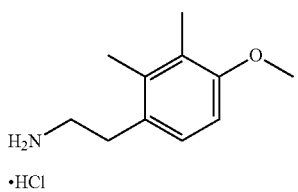

2-(4-Methoxy-2,3-dimethylphenyl)-ethylamine hydrochloride, from 4-methoxy-2,3-dimethylphenylacetonitrile, as a white powder, mp 229-235° C.; $^1$H NMR (DMSO-$d_6$) δ 8.15 (s, 3H), 6.97 (d, J=8.1 Hz, 2H), 6.75 (d, J=8.4 Hz, 1H), 3.74 (s, 3H), 2.86 (s, 4H), 2.18 (s, 3H), 2.18 (s, 3H); ESIMS m/z 179.0 ([M–Cl]$^+$).

Example 6

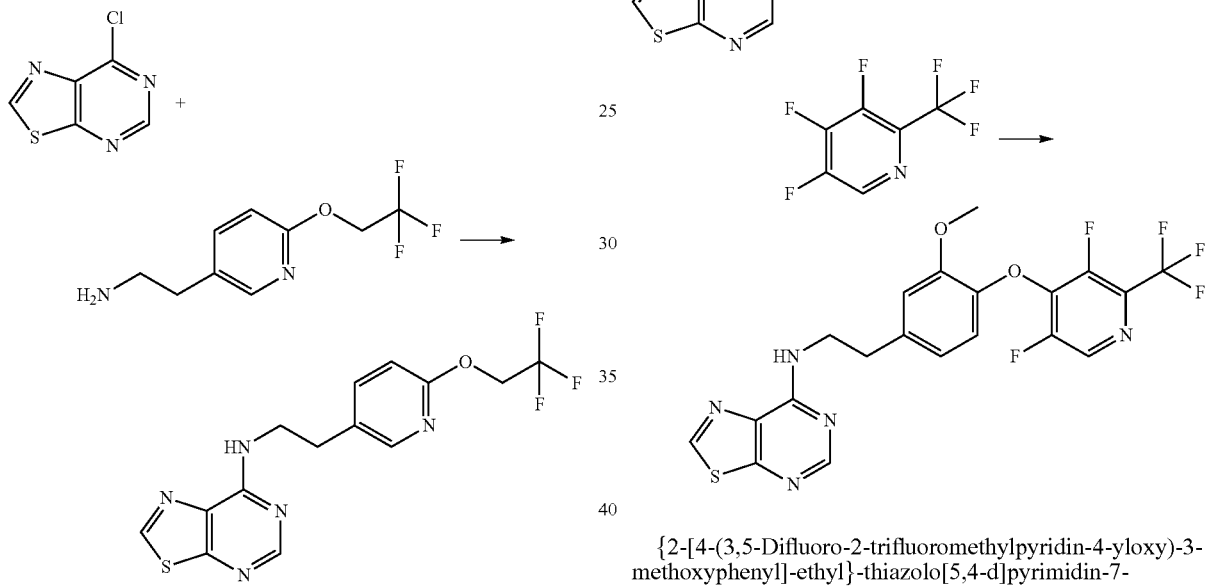

Thiazolo[5,4-d]pyrimidin-7-yl-{2-[6-(2,2,2-trifluoroethoxy)-pyridin-3-yl]-ethyl}-amine. 7-Chlorothiazolo[5,4-d]pyrimidine (0.17 g, 1.0 mmol) and 2-[6-(2,2,2-trifluoroethoxy)-pyridin-3-yl]-ethylamine (0.22 g, 1.0 mmol) were dissolved with magnetic stirring in DMF (4 mL) in a 25 mL round bottom flask equipped with a dry nitrogen line at 25° C. To the solution was added Et$_3$N (0.15 g, 1.5 mmol), and the mixture was heated on a steam bath for 1 minute (min). Another portion of 2-[6-(2,2,2-trifluoroethoxy)-pyridin-3-yl]-ethylamine (50 mg) was added, and heating was continued. After the starting materials were consumed, as assessed by TLC (1:1 Et$_2$O/hexane, SiO$_2$/glass plate), the reaction mixture was diluted with H$_2$O (100 mL), neutralized with 0.1 N HCl, and extracted into EtOAc (2×100 mL). The pooled organic fractions were concentrated in vacuo to provide 170 mg of a yellow solid. The solid was dissolved in a minimum amount of EtOAc and passed through a short SiO$_2$ column with EtOAc eluent. The appropriate fractions were pooled and concentrated in vacuo to provide thiazolo[5,4-d]pyrimidin-7-yl-{2-[6-(2,2,2-trifluoroethoxy)-pyridin-3-yl]-ethyl}-amine (Compound 4; 70 mg) as a pale yellow solid: mp 109-112° C.; $^1$H NMR (CDCl$_3$) 8.77 (s, 1H), 8.54 (s, 1H), 8.02 (d, J=2.0 Hz, 1H), 7.56 (dd, J=8.6, 2.6 Hz, 1H), 6.83 (d, J=8.6 Hz, 1H), 6.21 (br s, 1H), 4.74 (q, J=8.6 Hz, 2H), 3.90 (m, 2H), 2.98 (t, J=7.1 Hz, 2H); ESIMS m/z 356.2 ([M+H]$^+$).

Prepared in the same way:

Compound 34, 4-[1-(thiazolo[5,4-d]pyrimidin-7-ylamino)-ethyl]-phenol.

Compound 38, [2-(3-fluoro-4-methoxyphenyl)-ethyl]-thiazolo[5,4-d]pyrimidin-7-ylamine.

Example 7a

{2-[4-(3,5-Difluoro-2-trifluoromethylpyridin-4-yloxy)-3-methoxyphenyl]-ethyl}-thiazolo[5,4-d]pyrimidin-7-ylamine. 3,4,5-Trifluoro-2-trifluoromethylpyridine (0.61 g, 2.0 mmol) and 2-methoxy-4-[2-(thiazolo[5,4-d]pyrimidin-7-ylamino)-ethyl]-phenol (0.41 g, 2.0 mmol) were dissolved with magnetic stirring in DMF (8 mL) in a 25 mL round bottom flask equipped with a dry nitrogen line at 25° C. To the solution was added K$_2$CO$_3$ (2.0 g, 14.5 mmol). The reaction mixture was heated for 30 min on a steam bath, and carefully poured into a flask containing 0.1 N HCl (100 mL). The mixture was extracted with an equivolume of a 1:1 solution of Et$_2$O/pentane, and the layers were separated. The aqueous layer was washed with an equivolume of EtOAc, and the layers were separated. The EtOAc fraction was diluted with pentane (50 mL) and filtered, then combined with the Et$_2$O/pentane extract and concentrated in vacuo to afford a red gum (0.92 g). The gum was dissolved in minimal EtOAc and passed through a short SiO$_2$ column, with Et$_2$O as eluent. The appropriate fractions were pooled and concentrated in vacuo to provide {2-[4-(3,5-difluoro-2-trifluoromethylpyridin-4-yloxy)-3-methoxyphenyl]-ethyl}-thiazolo[5,4-d]pyrimidin-7-ylamine (Compound 32; 0.63 g) as viscous yellow oil, which solidified upon standing: mp 108-112° C.; $^1$H NMR (CDCl$_3$) δ 8.77 (s, 1H), 8.55 (s, 1H), 8.34 (s, 1H), 7.06 (d, J=7.2 Hz, 1H), 6.90-6.80 (m, 2H), 6.25 (br, 1H), 3.94 (dd, J=6.3, 6.3 Hz, 2H), 3.75 (s, 3H), 3.02 (t, J=6.9 Hz, 2H); ESIMS m/z 484.5 ([M+H]$^+$).

Prepared in the same way:

Compound 33, {2-[4-(3,5-difluoro-2-trifluoromethylpyridin-4-yloxy)-phenyl]-ethyl}-thiazolo[5,4-d]pyrimidin-7-ylamine.

Compound 36, {2-[4-(3,5-difluoro-4-trifluoromethylpyridin-2-yloxy)-phenyl]-ethyl}-thiazolo[5,4-d]pyrimidin-7-ylamine.

Compound 37, {2-[4-(4-amino-3,5,6-trifluoropyridin-2-yloxy)-3-methoxyphenyl]-ethyl}-thiazolo[5,4-d]pyrimidin-7-ylamine.

Example 7b

{2-[4-(3,5-Difluoro-2-trifluoromethylpyridin-4-yloxy)-phenyl]-1-methyl-ethyl}-thiazolo[5,4-d]pyrimidin-7-ylamine (Compound 14) was prepared by the same procedure as described in Example 7a, substituting DMSO for DMF to afford the product as a yellow oil: $^1$H NMR (400 MHz, CDCl$_3$) δ 8.77 (s, 1H), 8.52 (s, 1H), 8.44 (s, 1H), 7.25-7.20 (m, 2H), 6.95 (m, 2H), 5.99 (s, 1H), 4.68 (m, 1H), 3.05 (dd, J=13.6, 5.8 Hz, 1H), 2.87 (dd, J=13.6, 7.2 Hz, 1H), 1.31 (d, J=6.6 Hz, 3H); ESIMS m/z 467.8 ([M+H]$^+$).

Example 8

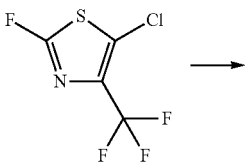

+

→

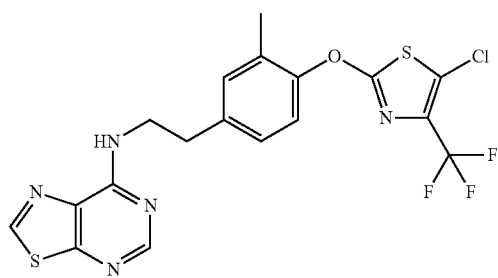

+

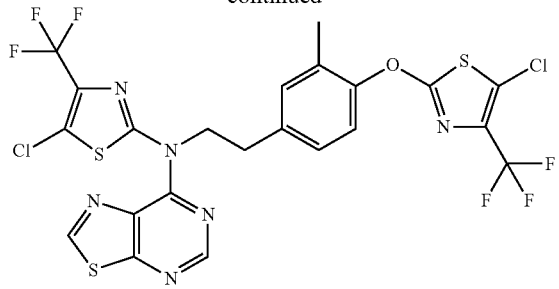

{2-[4-(5-Chloro-4-trifluoromethylthiazol-2-yloxy)-3-methylphenyl]-ethyl}-thiazolo[5,4-d]pyrimidin-7-ylamine, 2-Methyl-4-[2-(thiazolo[5,4-d]pyrimidin-7-ylamino)-ethyl]-phenol (0.2 g, 0.65 mmol) and 5-chloro-2-fluoro-4-trifluoromethylthiazole (0.14 g, 0.63 mmol) were dissolved with magnetic stirring in DMF (5 mL) in a 25 mL round bottom flask equipped with a dry nitrogen line at 25° C. To the solution was added NaH (60% dispersion in oil; 0.1 g, 2.5 mmol) and the reaction was stirred for 24 h. The reaction was diluted with 0.1 N HCl (100 mL) and washed with EtOAc (2×50 mL). The pooled organic fractions were filtered and concentrated in vacuo to afford a brown gum (0.33 g). The product was dissolved in minimal EtOAc and passed through a short SiO$_2$ column, with Et$_2$O as eluent. The appropriate fractions were pooled and concentrated in vacuo to provide {2-[4-(5-chloro-4-trifluoromethylthiazol-2-yloxy)-3-methylphenyl]-ethyl}-thiazolo[5,4-d]pyrimidin-7-ylamine (Compound 46; 80 mg) as a brown foam: ESIMS m/z 472.1 ([M+H]$^+$).

Other fractions were pooled to provide (5-chloro-4-trifluoromethylthiazol-2-yl)-{2-[4-(5-chloro-4-trifluoromethylthiazol-2-yloxy)-3-methylphenyl]-ethyl}-thiazolo[5,4-d]pyrimidin-7-ylamine (Compound 45; 20 mg) as a brown foam: ESIMS m/z 654.7 ([M+H]$^+$).

Prepared in the same way:

Compound 5, {2-[4-(2,3,5,6-tetrafluoropyridin-4-yloxy)-phenyl]-ethyl}-thiazolo[5,4-d]pyrimidin-7-ylamine.

Compound 7, thiazolo[5,4-d]pyrimidin-7-yl-{2-[4-(4-trifluoromethylpyridin-2-yloxy)-phenyl]-ethyl}-amine.

Compound 8, thiazolo[5,4-d]pyrimidin-7-yl-{2-[4-(3-trifluoromethylpyridin-2-yloxy)-phenyl]-ethyl}-amine.

Compound 13, {2-[2,5-dimethyl-4-(4-trifluoromethylpyridin-2-yloxy)-phenyl]-ethyl}-thiazolo[5,4-d]pyrimidin-7-ylamine.

Compound 16, 6-{4-[2-(thiazolo[5,4-d]pyrimidin-7-ylamino)-ethyl]-phenoxy}-4-trifluoromethyl-nicotinic acid methyl ester.

Compound 17, {2-[3-methoxy-4-(4-trifluoromethylpyridin-2-yloxy)-phenyl]-ethyl}-thiazolo[5,4-d]pyrimidin-7-ylamine.

Compound 18, {1-methyl-2-[4-(4-trifluoromethylpyridin-2-yloxy)-phenyl]-ethyl}-thiazolo[5,4-d]pyrimidin-7-ylamine.

Compound 23, {2-[3-methyl-4-(4-trifluoromethylpyridin-2-yloxy)-phenyl]-ethyl}-thiazolo[5,4-d]pyrimidin-7-ylamine.

Compound 24, {2-[3-methyl-4-(3-trifluoromethylpyridin-2-yloxy)-phenyl]-ethyl}-thiazolo[5,4-d]pyrimidin-7-ylamine.

Compound 27, 6-{2-bromo-4-[2-(thiazolo[5,4-d]pyrimidin-7-ylamino)-ethyl]-phenoxy}-4-trifluoromethyl-nicotinic acid methyl ester.

Compound 29, {2-[3-methoxy-4-(4-trifluoromethylpyridin-3-yloxy)-phenyl]-ethyl}-thiazolo[5,4-d]pyrimidin-7-ylamine.

Compound 31, {2-[3-methoxy-4-(3-trifluoromethylpyridin-4-yloxy)-phenyl]-ethyl}-thiazolo[5,4-d]pyrimidin-7-ylamine.

Compound 35, thiazolo[5,4-d]pyrimidin-7-yl-{1-[4-(4-trifluoromethylpyridin-2-yloxy)-phenyl]-ethyl}-amine.

Compound 41, {2-[3-fluoro-4-(4-trifluoromethylpyridin-2-yloxy)-phenyl]-ethyl}-thiazolo[5,4-d]pyrimidin-7-ylamine.

Compound 42, {2-[3-methoxy-4-(1-oxy-4-trifluoromethylpyridin-2-yloxy)-phenyl]-ethyl}-thiazolo[5,4-d]pyrimidin-7-ylamine.

Compound 47, {2-[3-methyl-4-(3-trifluoromethylpyridin-4-yloxy)-phenyl]-ethyl}-thiazolo[5,4-d]pyrimidin-7-ylamine.

Compound 48, {2-[4-(3,5-dichloro-2-trifluoromethylpyridin-4-yloxy)-3-methoxyphenyl]-ethyl}-thiazolo[5,4-d]pyrimidin-7-ylamine.

Compound 49, {2-[4-(3,5-dichloro-2-trifluoromethylpyridin-4-yloxy)-3-methylphenyl]-ethyl}-thiazolo[5,4-d]pyrimidin-7-ylamine.

Compound 50, thiazolo[5,4-d]pyrimidin-7-yl-{2-[4-(5-trifluoromethylpyridin-2-yloxy)-phenyl]-ethyl}-amine.

Compound 51, {2-[3-methoxy-4-(5-trifluoromethylpyridin-2-yloxy)-phenyl]-ethyl}-thiazolo[5,4-d]pyrimidin-7-ylamine.

Compound 52, thiazolo[5,4-d]pyrimidin-7-yl-{2-[4-(6-trifluoromethylpyrimidin-4-yloxy)-phenyl]-ethyl}-amine.

Compound 53, {2-[3-methyl-4-(6-trifluoromethylpyrimidin-4-yloxy)-phenyl]-ethyl}-thiazolo[5,4-d]pyrimidin-7-ylamine.

Compound 54, {2-[3-methoxy-4-(6-trifluoromethylpyrimidin-4-yloxy)-phenyl]-ethyl}-thiazolo[5,4-d]pyrimidin-7-ylamine.

Compound 59, {2-[2-methyl-4-(4-trifluoromethylpyridin-2-yloxy)-phenyl]-ethyl}-thiazolo[5,4-d]pyrimidin-7-ylamine.

Compound 60, {2-[2-fluoro-4-(4-trifluoromethylpyridin-2-yloxy)-phenyl]-ethyl}-thiazolo[5,4-d]pyrimidin-7-ylamine.

Compound 61, {2-[4-(3-fluoro-5-trifluoromethylpyridin-2-yloxy)-phenyl]-ethyl}-thiazolo[5,4-d]pyrimidin-7-ylamine.

Compound 63, {2-[2-fluoro-4-(6-trifluoromethylpyrimidin-4-yloxy)-phenyl]-ethyl}-thiazolo[5,4-d]pyrimidin-7-ylamine.

Example 9

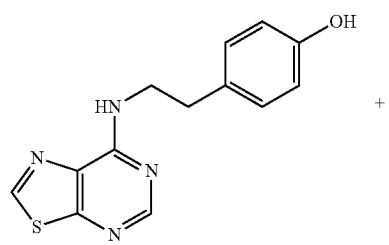

+

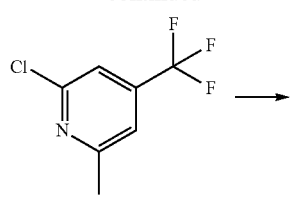

→

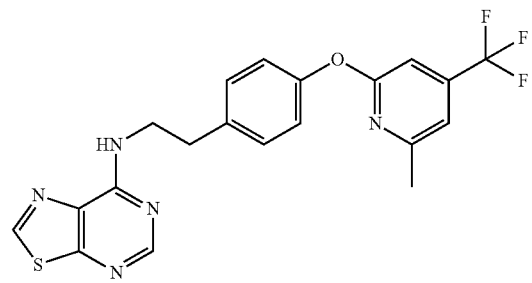

{2-[4-(6-Methyl-4-trifluoromethylpyridin-2-yloxy)-phenyl]-ethyl}-thiazolo[5,4-d]pyrimidin-7-ylamine. 4-[2-(Thiazolo[5,4-d]pyrimidin-7-ylamino)-ethyl]-phenol (0.1 g, 0.37 mmol) was dissolved with magnetic stirring in DMF (1 mL) in a microwave reactor tube, and then treated with NaH (60% dispersion in oil; 13 mg, 0.55 mmol). After bubbling had subsided, 2-chloro-6-methyl-4-trifluoromethylpyridine (86 mg, 0.44 mmol) was added and the reaction mixture was sealed and placed in a CEM Discover® microwave reactor and irradiated for 30 min, with heating to 150° C. After cooling, the reaction mixture was diluted with H$_2$O (5 mL) and partitioned into Et$_2$O (3×10 mL). The pooled organic fractions were diluted with an equal volume of pentane, washed with H$_2$O, dried (Na$_2$SO$_4$) and filtered through a SiO$_2$/Celite plug. The filtrate was concentrated in vacuo to provide a brown wax (126 mg). Prep RP-HPLC purification (CH$_3$CN/H$_2$O eluent; C18 column) afforded {2-[4-(6-methyl-4-trifluoromethylpyridin-2-yloxy)-phenyl]-ethyl}-thiazolo[5,4-d]pyrimidin-7-ylamine (Compound 62; 36 mg) as an off white powder: mp 111-112° C.; $^1$H NMR (CDCl$_3$) δ 8.76 (s, 1H), 8.55 (s, 1H), 7.31-7.29 (d, J=8.6 Hz, 2H), 7.11-7.07 (m, 3H), 6.83 (s, 1H), 6.22 (br s, 1H), 3.96-3.95 (br m, 2H), 3.05 (t, J=7.2 Hz, 2H), 2.51 (s, 3H); ESIMS m/z 432.2 ([M+H]$^+$).

Example 10

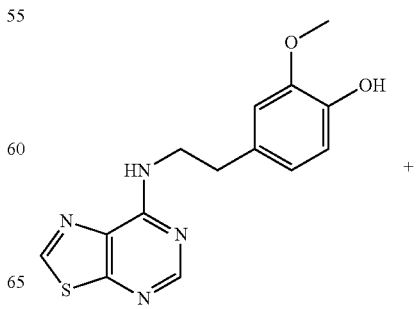

+

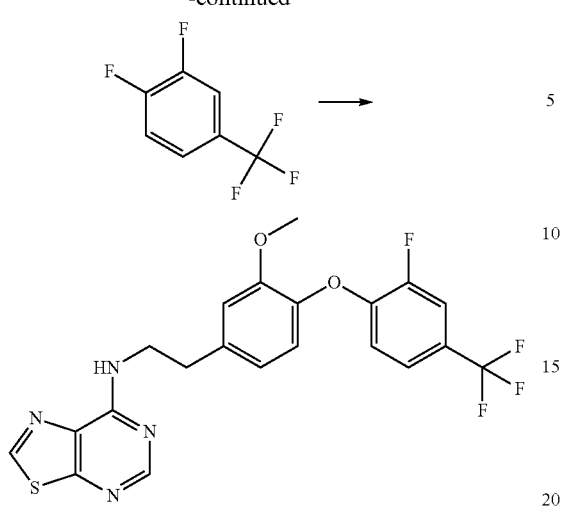

{2-[4-(2-Fluoro-4-trifluoromethylphenoxy)-3-methoxyphenyl]-ethyl}-thiazolo[5,4-d]pyrimidin-7-ylamine. 1,2-Difluoro-4-trifluoromethylbenzene (0.19 g, 1.0 mmol) and 2-methoxy-4-[2-(thiazolo[5,4-d]pyrimidin-7-ylamino)-ethyl]-phenol (0.3 g, 1.0 mmol) were dissolved with magnetic stirring in DMF (4 mL) in a 25 mL round bottom flask equipped with a dry nitrogen line at 25° C. To the solution was added NaH (60% dispersion in oil; 90 mg, 2.25 mmol). After stirring at room temperature for 72 h, the reaction mixture was heated on a steam bath for 2 h, and carefully poured into a flask containing 0.1 N HCl (100 mL). The mixture was extracted with EtOAc (3×50 mL). The pooled organic fractions were filtered and concentrated in vacuo to afford a yellow solid (0.11 g). The product was dissolved in minimal $CH_2Cl_2$ and passed through a short $SiO_2$ column with $Et_2O$ as eluent. The appropriate fractions were pooled and concentrated in vacuo to provide {2-[4-(2-fluoro-4-trifluoromethylphenoxy)-3-methoxyphenyl]-ethyl}-thiazolo[5,4-d]pyrimidin-7-ylamine (Compound 30; 70 mg) as a colorless oil in approximately 80% purity as determined by $^1$H NMR spectrometry. $^1$H NMR (CDCl$_3$) δ 8.77 (s, 1H), 8.55 (s, 1H), 7.42 (dd, J=10.8, 2.1 Hz, 1H), 7.01-6.75 (m, 5H), 6.24 (br, 1H), 3.96 (m, 2H), 3.78 (s, 3H), 3.04 (t, J=7.1 Hz, 2H); ESIMS m/z 465.2 ([M+H]$^+$).

Example 11

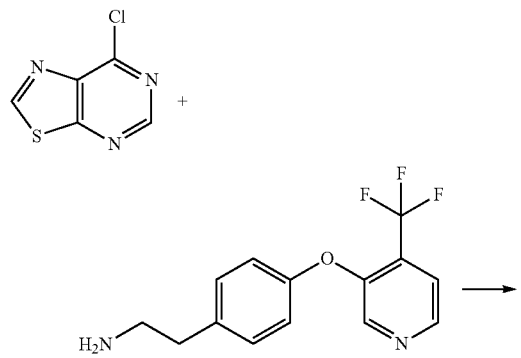

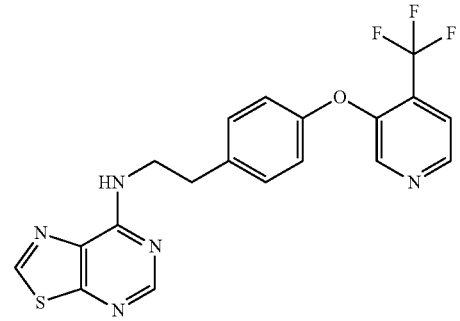

Thiazolo[5,4-d]pyrimidin-7-yl-{2-[4-(4-trifluoromethylpyridin-3-yloxy)-phenyl]-ethyl}-amine. 2-[4-(4-Trifluoromethylpyridin-3-yloxy)-phenyl]-ethylamine (0.25 g, 0.88 mmol), 7-chlorothiazolo[5,4-d]pyrimidine (0.15 g, 0.88 mmol) and $K_2CO_3$ (3 g) were dissolved with magnetic stirring in DMSO (7 mL) in a 25 mL round bottom flask equipped with a dry nitrogen line at 25° C. After placing the flask in a sonication bath for 3 min, the reaction mixture was heated on a steam bath for 2 min. The mixture was filtered, and the filter cake was washed with acetone. The combined filtrates were diluted with 0.15 N HCl (100 mL) and washed successively with $Et_2O$ (2×50 mL) and EtOAc (2×50 mL). The pooled organic fractions were filtered and concentrated in vacuo to provide 0.27 g of a yellow gum. The gum was dissolved in a small volume of EtOAc and passed through a short $SiO_2$ column with 1% MeOH/EtOAc as eluent. The appropriate fractions were pooled and concentrated in vacuo to provide a clear colorless oil (0.17 g). Trituration in $Et_2O$ followed by decanting of the solvent afforded thiazolo[5,4-d]pyrimidin-7-yl-{2-[4-(4-trifluoromethylpyridin-3-yloxy)-phenyl]-ethyl}-amine (Compound 43; 170 mg) as a yellow solid: mp 83-87° C.; $^1$H NMR (400 MHz, CDCl$_3$) δ 8.77 (s, 1H), 8.55 (s, 1H), 8.50 (s, 1H), 8.34 (s, 1H), 7.54 (s, 1H), 7.30 (d, J=8.6 Hz, 2H), 7.06-6.99 (m, 2H), 6.22 (s, 1H), 3.94 (dd, J=12.9, 6.5 Hz, 2H), 3.04 (t, J=7.1 Hz, 2H); ESIMS m/z 418.2 ([M+H]$^+$).

Example 12

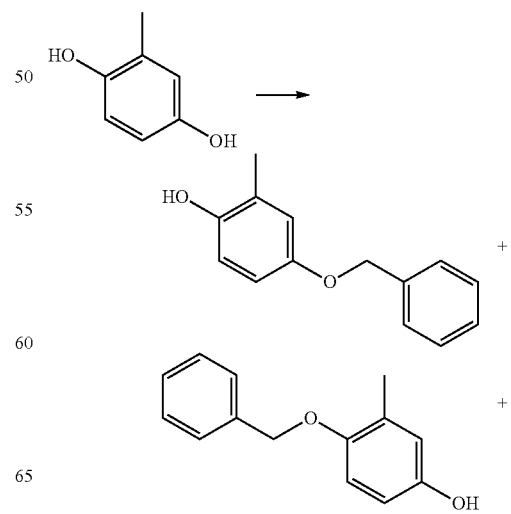

47

-continued

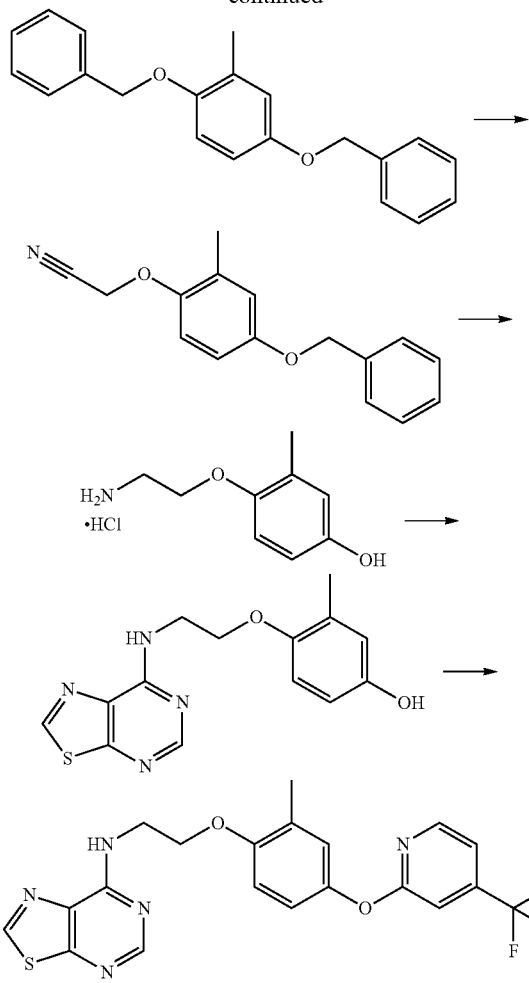

3-Methyl-4-[2-(thiazolo[5,4-d]pyrimidin-7-ylamino)-ethoxy]-phenol. 4-(2-Aminoethoxy)-3-methylphenol hydrochloride (0.30 g, 1.5 mmol), 7-chlorothiazolo[5,4-d]pyrimidine (0.25 g, 1.5 mmol), and $Et_3N$ (300 mg, 3 mmol) were dissolved with magnetic stirring in DMF (6 mL) in a 25 mL round bottom flask equipped with a dry nitrogen line at 25° C. After 24 h, the reaction mixture was diluted with $H_2O$ (120 mL), and treated with 2 N HCl to adjust the pH to 5. After 24 h, a dark yellow solid precipitated and was removed by filtration. The filtrate was extracted with EtOAc (2×50 mL), and the pooled organic fractions were filtered and concentrated in vacuo to afford 3-methyl-4-[2-(thiazolo[5,4-d]pyrimidin-7-ylamino)-ethoxy]-phenol (Compound 22; 0.13 g) as a yellow powder, which was used without further purification in the next step: ESIMS m/z 303.0 ([M+H]$^+$).

Example 13

{2-[2-Methyl-4-(4-trifluoromethylpyridin-2-yloxy)-phenoxy]-ethyl}-thiazolo[5,4-d]pyrimidin-7-ylamine. 3-Methyl-4-[2-(thiazolo[5,4-d]pyrimidin-7-ylamino)-ethoxy]-phenol (0.13 g, 0.43 mmol) and 2-fluoro-4-trifluoromethylpyridine (0.1 g, 0.6 mmol) were dissolved with magnetic stirring in DMF (4 mL) in a 25 mL round bottom flask equipped with a dry nitrogen line at 25° C. To the solution was added NaH (60% dispersion in oil; 60 mg, 1.5 mmol) and the reaction mixture was stirred for 2 h. The reaction was diluted with $H_2O$ (100 mL), and 2 N HCl was added to adjust the pH to 6. After 24 h, a pale brown film had formed on the flask wall. The aqueous supernatant was extracted with $Et_2O$ (2×50 mL), and the pooled aqueous fractions were combined with the brown film, and then concentrated in vacuo to yield 0.2 g of a tan semi-solid. Recrystallization from hexane afforded {2-[2-methyl-4-(4-trifluoromethylpyridin-2-yloxy)-phenoxy]-ethyl}-thiazolo[5,4-d]pyrimidin-7-ylamine (Compound 9; 70 mg) as white crystals: mp 107-111° C.; $^1$H NMR (600 MHz, CDCl$_3$) δ 8.78 (s, 1H), 8.53 (s, 1H), 8.29 (d, J=5.2 Hz, 1H), 7.17-7.11 (m, 1H), 7.08 (s, 1H), 6.92-6.90 (m, 2H), 6.85 (d, J=8.7 Hz, 1H), 6.56 (s, 1H), 4.29-4.20 (m, 2H), 4.11 (d, J=4.4 Hz, 2H), 2.25 (s, 3H); ESIMS m/z 448.1 ([M+H]$^+$).

Preparation 4

Step 1. 4-Benzyloxy-2-methylphenol. 2-Methylbenzene-1,4-diol (12.4 g, 0.1 mol) was dissolved in acetone (200 mL) in a 500 mL round bottom flask equipped with magnetic stirrer, reflux condenser and dry nitrogen line. To the solution was added $K_2CO_3$ (20.5 g), followed by benzyl bromide (12.2 mL, 0.1 mol) with vigorous stirring. After stirring at room temperature for 72 h, the reaction mixture was filtered and concentrated in vacuo. The residue was partitioned between slightly acidic $H_2O$ (pH adjusted to 5 with 0.1 N HCl) and a 1:1 mixture of $Et_2O$/pentane. The organic layer was filtered and concentrated in vacuo to provide a black oil (20.66 g). The oil was extracted with isopentane (3×150 mL) and the pooled isopentane fractions were concentrated in vacuo to provide an orange oil (10 g); the dark insoluble residue was set aside. The orange oil was passed over a $SiO_2$ column with $Et_2O$/pentane (1:1) eluent. The appropriate fractions were pooled and concentrated in vacuo to provide 1,4-bisbenzyloxy-2-methylbenzene (7.0 g) as a pale yellow oil, which solidified on standing: mp 42-43° C.; $^1$H NMR (400 MHz, CDCl$_3$) δ 7.46-7.41 (m, 4H), 7.38 (ddd, J=7.9, 5.0, 3.3 Hz, 4H), 7.34-7.29 (m, 2H), 6.84 (d, J=2.8 Hz, 1H), 6.80 (d, J=8.8 Hz, 1H), 6.73 (dd, J=8.8, 3.0 Hz, 1H), 5.02 (s, 2H), 5.00 (s, 2H), 2.27 (s, 3H); ESIMS m/z 304.2 ([M+H]$^+$).

The dark insoluble residue from above was passed over a $SiO_2$ column with $Et_2O$/pentane (1:2) as eluent. The appropriate fractions were pooled and concentrated in vacuo to provide 7.2 g of 4-benzyloxy-2-methylphenol and 4-benzyloxy-3-methylphenol (approximately 1:1 mixture of monobenzylated isomers) as an orange solid, which was used in the next step without further purification. $^1$H NMR (600 MHz, CDCl$_3$) δ 7.45-7.39 (m, 4H), 7.37 (ddd, J=7.9, 5.0, 1.7 Hz, 4H), 7.33-7.27 (m, 2H), 6.77 (s, 1H), 6.74 (d, J=8.6 Hz, 1H), 6.69-6.67 (m, 2H), 6.66 (dd, J=4.6, 1.8 Hz, 1H), 6.60-6.56 (m, 1H), 5.01 (s, 2H), 4.99 (s, 2H), 4.41 (s, 1H), 4.39 (s, 1H), 2.27-2.18 (m, 6H); ESIMS m/z 215.1 ([M+H]$^+$).

Step 2. (4-Benzyloxy-2-methylphenoxy)-acetonitrile. 4-Benzyloxy-2-methylphenol and 4-benzyloxy-3-methylphenol (approximately 1:1 mixture of monobenzylated isomers from previous step; 5.76 g, 27 mmol) and bromoacetonitrile (3.24 g, 27 mmol) were dissolved in THF (100 mL) in a 500 mL round bottom flask equipped with a magnetic stir bar, reflux condenser and dry nitrogen line. The solution was treated with NaH (60% dispersion in oil; 1.4 g, 35 mmol) and stirred at room temperature overnight. The reaction mixture was diluted with DMF (20 mL), and then stirred another 2 h at room temperature. The reaction mixture was concentrated in vacuo, and then taken up in $H_2O$ (200 mL). After adjusting the pH to 4 with 2 N HCl, the aqueous layer was washed with an equivolume of $Et_2O$/pentane (1:1). The organic layer was concentrated in vacuo to provide a yellow-brown oil (6.45 g).

The oil was subjected to Prep RP-HPLC to provide a slightly purified product, after pooling appropriate fractions. This product was extracted with boiling isopentane (3×100 mL), and the pooled isopentane fractions were concentrated in vacuo to provide 2.25 g of (4-benzyloxy-2-methylphenoxy)-acetonitrile (isomer A) and (4-benzyloxy-3-methylphenoxy)-acetonitrile (isomer B), in an approximately 2:1 mixture of A:B (determined by $^1$H NMR spectral integrations), as a pale yellow oil. The insoluble residue was boiled up in pentane, decanted, and cooled to room temperature. After 24 h, crystals had formed. The supernatant was decanted, and found to contain 750 mg of isomers A and B in a 1:3 ratio ($^1$H NMR spectral analysis). The crystals were found to be the desired isomer A. Successive pentane digestions of the crude residues and crystallization eventually led to the recovery of 1.95 g of the highly enriched (4-benzyloxy-2-methylphenoxy)-acetonitrile (isomer A). $^1$H NMR (600 MHz, CDCl$_3$) δ 7.41 (d, J=7.0 Hz, 2H), 7.37 (dd, J=10.1, 5.0 Hz, 2H), 7.31 (t, J=7.2 Hz, 1H), 6.84 (m, 2H), 6.76 (dd, J=8.8, 3.1 Hz, 1H), 5.02 (s, 2H), 4.69 (s, 2H), 2.22 (s, 3H); ESIMS m/z 254.2 ([M+H]$^+$).

Step 3. 4-(2-Aminoethoxy)-3-methylphenol hydrochloride. (4-Benzyloxy-2-methylphenoxy)-acetonitrile (1.95 g, 7.7 mmol) was dissolved in absolute EtOH (100 mL) in a Parr bottle. The solution was treated with conc. HCl (1.55 g) and 10% Pd/C (0.3 g), degassed, charged with H$_2$ (55 psig), and shaken for 72 h. The suspension was filtered and concentrated in vacuo to afford 4-(2-aminoethoxy)-3-methylphenol hydrochloride (1.92 g) as a beige solid, which was used without further purification in the next step: EIMS m/z 167 ([M–HCl]$^+$).

Also prepared by Preparation 4, Step 3.

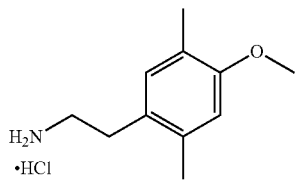

2-(4-Methoxy-2,5-dimethylphenyl)-ethylamine hydrochloride, from (4-methoxy-2,5-dimethylphenyl)-acetonitrile: ESIMS m/z 180.2 ([M–Cl]$^+$).

Example 14

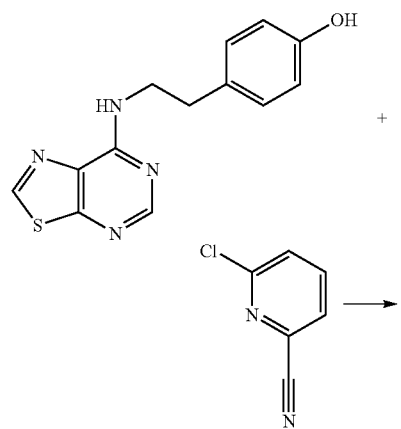

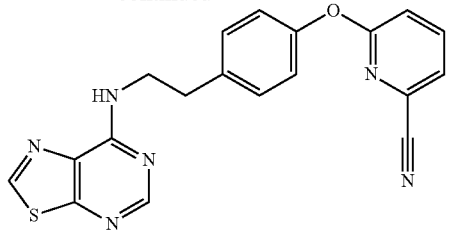

6-{2-Methoxy-4-[2-(thiazolo[5,4-d]pyrimidin-7-ylamino)-ethyl]-phenoxy}-pyridine-2-carbonitrile. To a solution of 4-[2-(thiazolo[5,4-d]pyrimidin-7-ylamino)-ethyl]-phenol (0.26 g, 0.96 mmol) and 6-chloropyridine-2-carbonitrile (0.14 g, 1.0 mmol) in DMF (8 mL) in a 25 mL round bottom flask equipped with a dry nitrogen line at 25° C. was added potassium tert-butoxide (1 M solution in THF; 1.0 mL; 1.0 mmol) with magnetic stirring. After stirring at room temperature for 15 min, the reaction mixture was heated on a steam bath for 15 min. The reaction mixture then was diluted with H$_2$O (100 mL) and neutralized by addition of HCl (aq 2 N). The precipitate which formed was collected by suction filtration, washed with H$_2$O and air dried on the filter to afford 200 mg of an orange solid. This product was taken up in a boiling mixture of EtOAc and MeOH (60 mL), treated with decolorizing carbon and filtered. The filtrate was concentrated in vacuo to afford 70 mg of a pale yellow film. Purification by column chromatography (SiO$_2$; EtOAc/hexane eluent) provided 6-{2-methoxy-4-[2-(thiazolo[5,4-d]pyrimidin-7-ylamino)-ethyl]-phenoxy}-pyridine-2-carbonitrile (Compound 6; 17 mg) as a yellow gum; GC-MS m/z 374 [M$^+$].

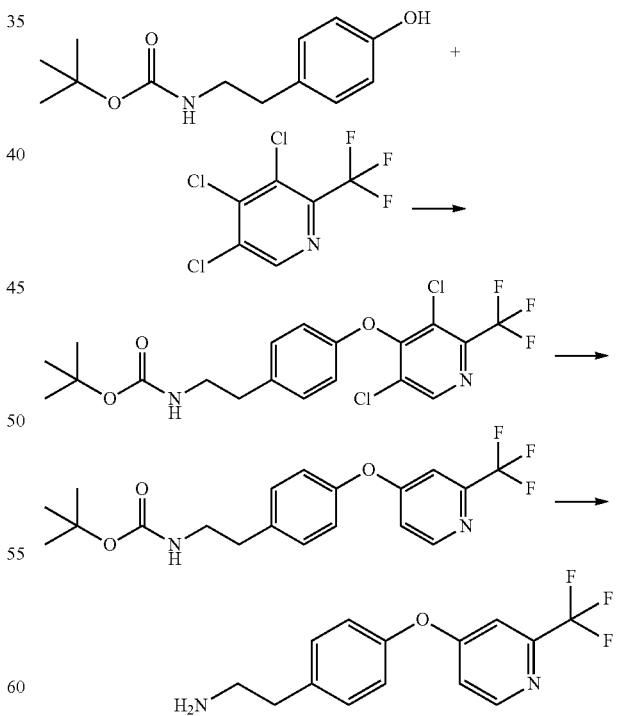

Preparation 5

Step 1. {2-[4-(3,5-Dichloro-2-trifluoromethylpyridin-4-yloxy)-phenyl]-ethyl}-carbamic acid tert-butyl ester. 3,4,5-

Trichloro-2-trifluoromethylpyridine (0.75 g, 3 mmol) and [2-(4-hydroxyphenyl)-ethyl]carbamic acid tert-butyl ester (0.72 g, 3 mmol) were dissolved with magnetic stirring in DMSO (7 mL) in a 25 mL round bottom flask equipped with a reflux condenser and a dry nitrogen line at 25° C. To the mixture was added $K_2CO_3$ (3 g, 21.7 mmol). The reaction mixture was heated at 100° C. for 3 min and stirred at 25° C. for an additional 36 h. The reaction mixture was filtered, and the filter cake was washed with EtOAc. The pooled organic fractions were concentrated in vacuo to afford a white gel, which was diluted with $H_2O$ (150 mL) to precipitate a white crystalline solid. The product was collected by suction filtration and air-dried to afford {2-[4-(3,5-dichloro-2-trifluoromethylpyridin-4-yloxy)-phenyl]-ethyl}-carbamic acid tert-butyl ester (1.3 g) as a white crystalline solid: mp 137-140° C.; ESIMS m/z 451 [(M−H)⁻].

Step 2. {2-[4-(2-Trifluoromethylpyridin-4-yloxy)-phenyl]-ethyl}-carbamic acid tert-butyl ester. {2-[4-(3,5-Dichloro-2-trifluoromethylpyridin-4-yloxy)-phenyl]-ethyl}-carbamic acid tert-butyl ester (0.78 g, 1.73 mmol) and $Et_3N$ (350 mg, 3.46 mmol) were dissolved in EtOH (100 mL) in a 500 mL Parr bottle under nitrogen. To the reaction mixture was added palladium hydroxide ($Pd(OH)_2$; 0.45 g) and the reactor was charged with $H_2$ (50 psi) and shaken for 24 h. The reaction mixture was filtered and concentrated in vacuo. The residue was partitioned between $Et_2O$ (50 mL) and 0.1 N HCl (50 mL), and the aqueous layer was washed again with $Et_2O$. The pooled organic fractions were filtered and concentrated in vacuo to afford {2-[4-(2-trifluoromethylpyridin-4-yloxy)-phenyl]-ethyl}-carbamic acid tert-butyl ester (0.63 g) as a pale yellow oil. ¹H NMR and MS analyses (ESIMS m/z 382) indicated the product contained approximately 14% {2-[4-(3-chloro-2-trifluoromethylpyridin-4-yloxy)-phenyl]-ethyl}-carbamic acid tert-butyl ester (EIMS m/z 416). The product was carried onto the next step without further purification.

Step 3. 2-[4-(2-Trifluoromethylpyridin-4-yloxy)-phenyl]-ethylamine. {2-[4-(2-Trifluoromethylpyridin-4-yloxy)-phenyl]-ethyl}-carbamic acid tert-butyl ester (0.79 g, 2 mmol) was dissolved in $CH_2Cl_2$ (20 mL) in a 50 mL round bottom flask equipped with a reflux condenser and a dry nitrogen line at 25° C. Trifluoroacetic acid (2 g) was added, and after stirring at room temperature for 6 h, the reaction mixture was concentrated in vacuo. The residue was partitioned between EtOAc (75 mL) and $H_2O$ (50 mL; pH adjusted to 10 by addition of a solution of satd aq $NaHCO_3$). The organic fraction was separated, filtered and concentrated in vacuo to afford 2-[4-(2-trifluoromethylpyridin-4-yloxy)-phenyl]-ethylamine (0.52 g) that quickly became a viscous black tar. The product was used immediately without further purification.

Preparation 6

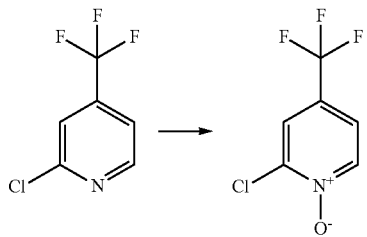 [SMILES: FC(F)(F)c1ccnc(Cl)c1 ; [O-][n+]1ccc(C(F)(F)F)cc1Cl]

2-Chloro-4-trifluoromethylpyridine N-oxide. To a solution of 2-chloro-4-trifluoromethylpyridine (1.81 g, 10 mmol) in trifluoroacetic acid (12 mL) was added 30% hydrogen peroxide (8 mL), and the mixture was stirred at 50° C. over a weekend. The reaction mixture was poured into ice-cold $H_2O$, neutralized with solid $Na_2CO_3$ with stirring, and extracted with EtOAc three times. The combined organic layer was dried over anhydrous $Na_2SO_4$, filtered, concentrated, and dried to give analytically pure 2-chloro-4-trifluoromethylpyridine N-oxide (1.67 g) as a brown oil: ¹H NMR ($CDCl_3$) δ 8.45 (d, J=6.9 Hz, 1H), 7.77 (d, J=2.4 Hz, 1H), 7.47 (dd, J=6.9, 2.4 Hz, 1H); GC-MS m/z 197 ([M]⁺).

Table 1 shows representative compounds of formula (I-A) and (I-B), together with characterizing data (mass spectrometry or other), as well as preparative method, electrophile or other reactant and amine or other reactant.

TABLE 1

Examples of compounds of formula (I-A) and (I-B).

| Compound | Structure |
| --- | --- |
| 1 | 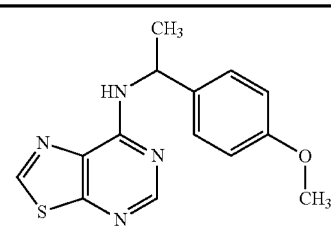 |
| 2 | 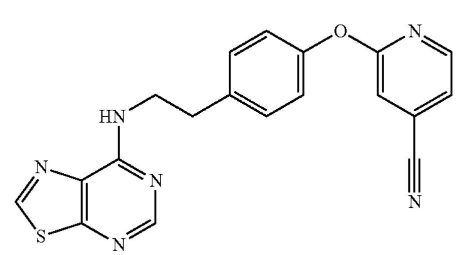 [SMILES: N#Cc1ccnc(Oc2ccc(CCNc3ncnc4scnc34)cc2)c1] |

TABLE 1-continued

Examples of compounds of formula (I-A) and (I-B).

| Compound | Structure |
|---|---|
| 3 | (thiazolo[5,4-d]pyrimidin-7-yl)-NH-CH₂CH₂-(4-hydroxyphenyl) |
| 4 | (thiazolo[5,4-d]pyrimidin-7-yl)-NH-CH₂CH₂-(6-(2,2,2-trifluoroethoxy)pyridin-3-yl) |
| 5 | (thiazolo[5,4-d]pyrimidin-7-yl)-NH-CH₂CH₂-(4-((2,3,5,6-tetrafluoropyridin-4-yl)oxy)phenyl) |
| 6 | (thiazolo[5,4-d]pyrimidin-7-yl)-NH-CH₂CH₂-(4-((6-cyanopyridin-2-yl)oxy)phenyl) |
| 7 | (thiazolo[5,4-d]pyrimidin-7-yl)-NH-CH₂CH₂-(4-((4-(trifluoromethyl)pyridin-2-yl)oxy)phenyl) |

TABLE 1-continued

Examples of compounds of formula (I-A) and (I-B).

| Compound | Structure |
|---|---|
| 8 | 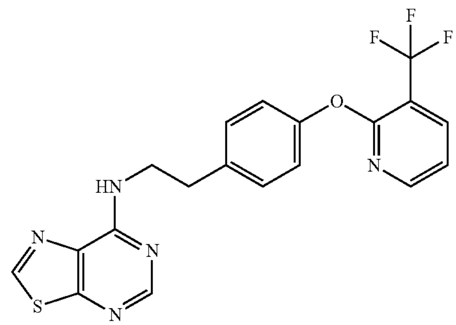 [SMILES: FC(F)(F)c1cccnc1Oc1ccc(CCNc2ncnc3scnc23)cc1] |
| 9 | 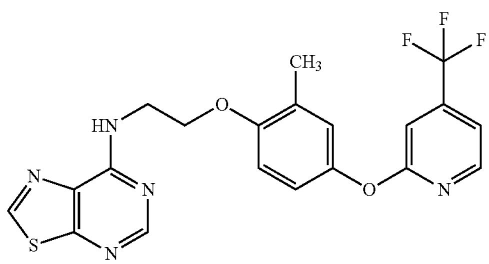 [SMILES: Cc1cc(Oc2cc(C(F)(F)F)ccn2)ccc1OCCNc1ncnc2scnc12] |
| 10 | 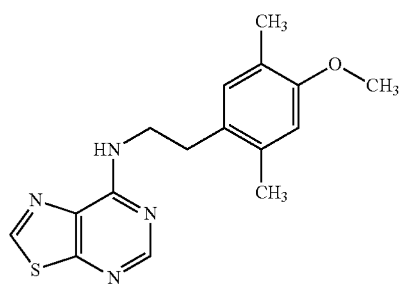 [SMILES: COc1cc(C)c(CCNc2ncnc3scnc23)cc1C] |
| 11 | 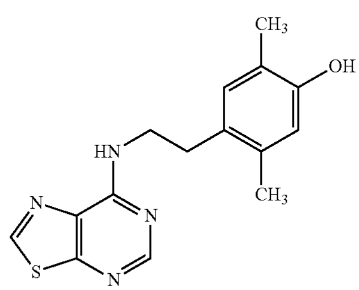 [SMILES: Cc1cc(CCNc2ncnc3scnc23)c(C)cc1O] |
| 12 | 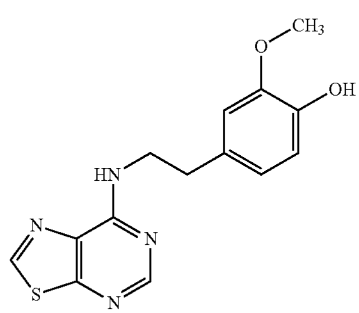 [SMILES: COc1cc(CCNc2ncnc3scnc23)ccc1O] |

TABLE 1-continued

Examples of compounds of formula (I-A) and (I-B).

| Compound | Structure |
|---|---|
| 13 | 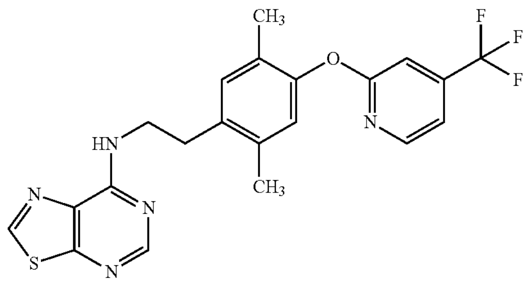 [SMILES: Cc1cc(Oc2cc(C(F)(F)F)ccn2)c(C)cc1CCNc1ncnc2scnc12] |
| 14 | 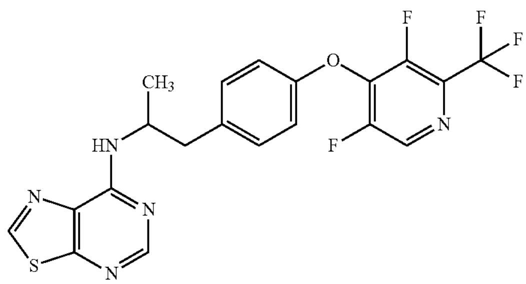 [SMILES: CC(Cc1ccc(Oc2c(F)cnc(C(F)(F)F)c2F)cc1)Nc1ncnc2scnc12] |
| 15 | 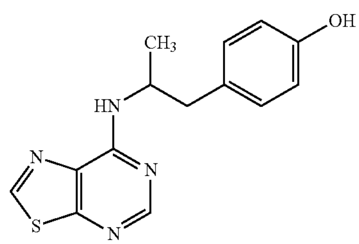 [SMILES: CC(Cc1ccc(O)cc1)Nc1ncnc2scnc12] |
| 16 | 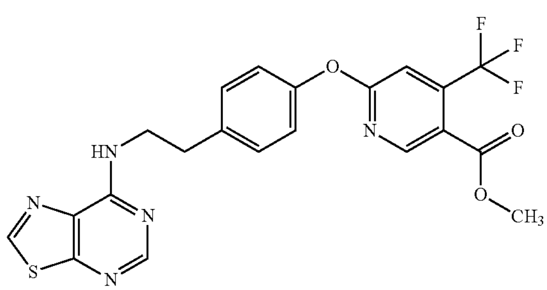 [SMILES: COC(=O)c1cnc(Oc2ccc(CCNc3ncnc4scnc34)cc2)cc1C(F)(F)F] |
| 17 | 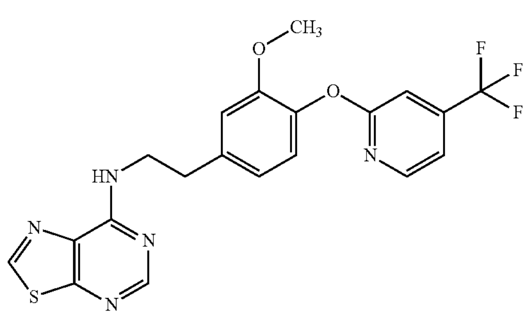 [SMILES: COc1cc(CCNc2ncnc3scnc23)ccc1Oc1cc(C(F)(F)F)ccn1] |

TABLE 1-continued

Examples of compounds of formula (I-A) and (I-B).

| Compound | Structure |
|---|---|
| 18 | [thiazolo[5,4-d]pyrimidin-7-yl]-NH-CH(CH₃)-CH₂-[4-(4-trifluoromethyl-pyridin-2-yloxy)phenyl] |
| 19 | [thiazolo[5,4-d]pyrimidin-7-yl]-NH-CH₂CH₂-[3-methyl-4-methoxyphenyl] |
| 20 | [thiazolo[5,4-d]pyrimidin-7-yl]-NH-CH₂CH₂-[3-methyl-4-hydroxyphenyl] |
| 21 | [thiazolo[5,4-d]pyrimidin-7-yl]-NH-CH₂CH₂-[3-bromo-4-methoxyphenyl] |
| 22 | [thiazolo[5,4-d]pyrimidin-7-yl]-NH-CH₂CH₂-O-[2-methyl-4-hydroxyphenyl] |

TABLE 1-continued

Examples of compounds of formula (I-A) and (I-B).

| Compound | Structure |
|---|---|
| 23 | 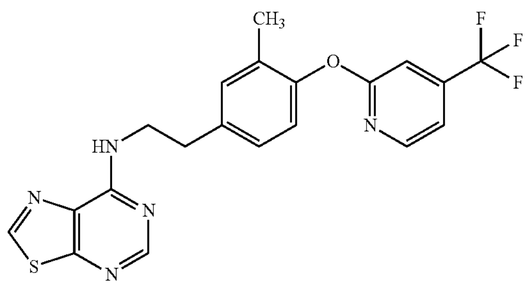 [SMILES: Cc1cc(CCNc2ncnc3scnc23)ccc1Oc1cc(C(F)(F)F)ccn1] |
| 24 | 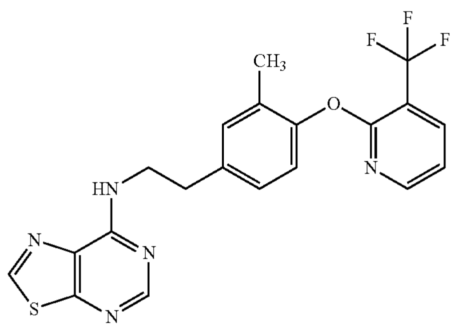 [SMILES: Cc1cc(CCNc2ncnc3scnc23)ccc1Oc1ncccc1C(F)(F)F] |
| 25 | 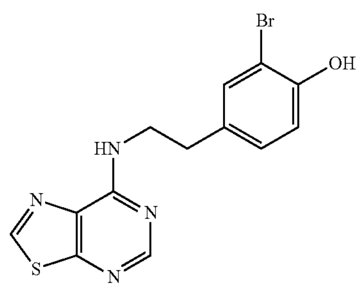 [SMILES: Oc1ccc(CCNc2ncnc3scnc23)cc1Br] |
| 26 | 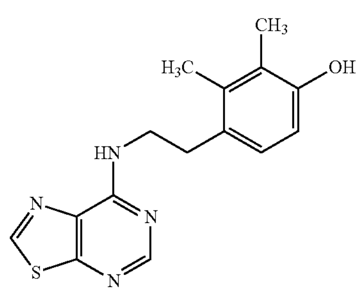 [SMILES: Cc1c(O)ccc(CCNc2ncnc3scnc23)c1C] |
| 27 | 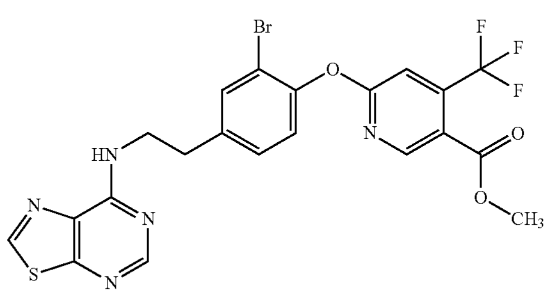 [SMILES: COC(=O)c1cnc(Oc2ccc(CCNc3ncnc4scnc34)cc2Br)cc1C(F)(F)F] |

TABLE 1-continued

Examples of compounds of formula (I-A) and (I-B).

| Compound | Structure |
|----------|-----------|
| 28 | 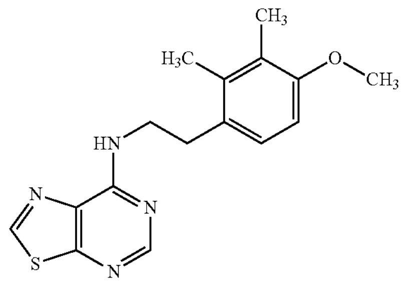 [SMILES: COc1ccc(CCNc2ncnc3scnc23)c(C)c1C] |
| 29 | 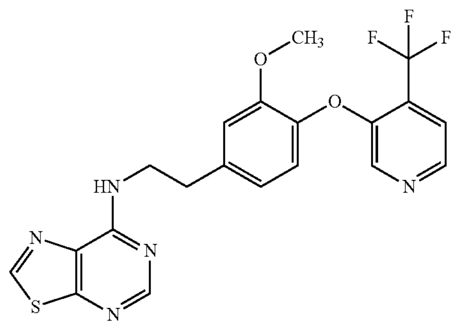 [SMILES: COc1cc(CCNc2ncnc3scnc23)ccc1Oc1cnccc1C(F)(F)F] |
| 30 | 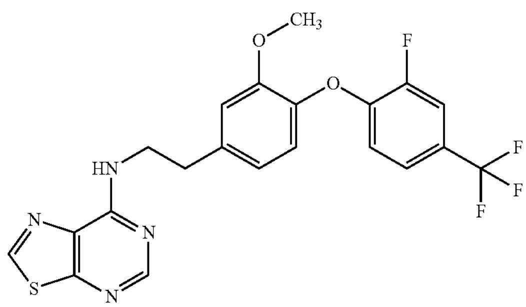 [SMILES: COc1cc(CCNc2ncnc3scnc23)ccc1Oc1ccc(C(F)(F)F)cc1F] |
| 31 | 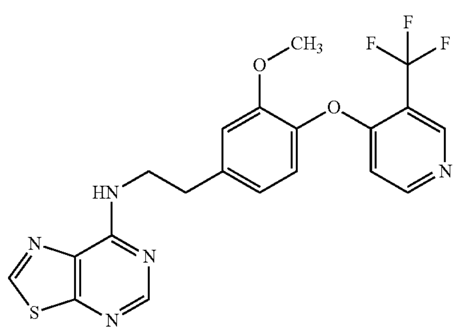 [SMILES: COc1cc(CCNc2ncnc3scnc23)ccc1Oc1ccncc1C(F)(F)F] |
| 32 | 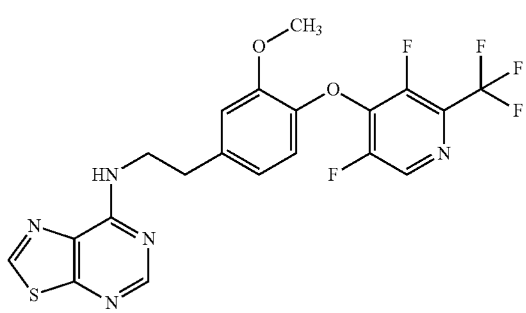 [SMILES: COc1cc(CCNc2ncnc3scnc23)ccc1Oc1c(F)cnc(C(F)(F)F)c1F] |

TABLE 1-continued

Examples of compounds of formula (I-A) and (I-B).

| Compound | Structure |
|---|---|
| 33 | 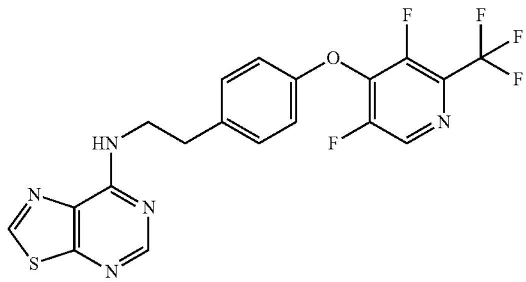 [SMILES: Fc1cnc(C(F)(F)F)c(F)c1Oc1ccc(CCNc2ncnc3scnc23)cc1] |
| 34 | 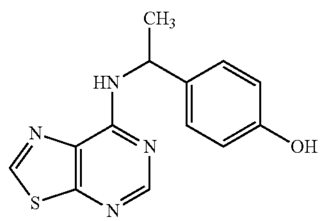 [SMILES: CC(Nc1ncnc2scnc12)c1ccc(O)cc1] |
| 35 | 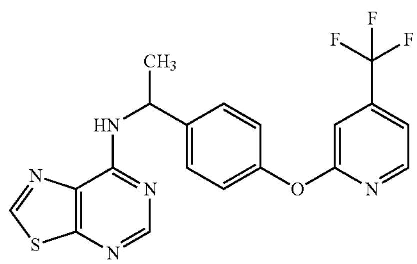 [SMILES: CC(Nc1ncnc2scnc12)c1ccc(Oc2cc(C(F)(F)F)ccn2)cc1] |
| 36 | 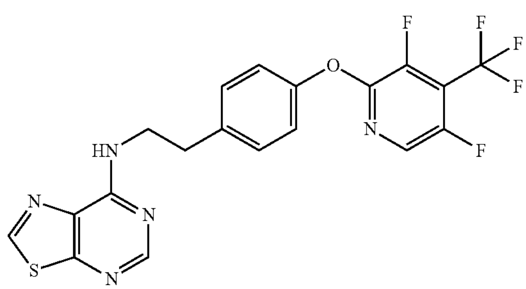 [SMILES: Fc1cnc(Oc2ccc(CCNc3ncnc4scnc34)cc2)c(F)c1C(F)(F)F] |
| 37 | 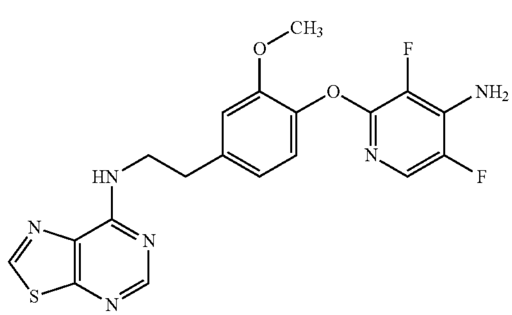 [SMILES: COc1cc(CCNc2ncnc3scnc23)ccc1Oc1ncc(F)c(N)c1F] |

TABLE 1-continued

Examples of compounds of formula (I-A) and (I-B).

| Compound | Structure |
|---|---|
| 38 | (thiazolo[5,4-d]pyrimidin-7-yl)-NH-CH₂CH₂-(3-fluoro-4-methoxyphenyl) |
| 39 | (thiazolo[5,4-d]pyrimidin-7-yl)-NH-CH₂CH₂-(3-fluoro-4-hydroxyphenyl) |
| 40 | (thiazolo[5,4-d]pyrimidin-7-yl)-NH-CH₂CH₂-(4-{[2-(trifluoromethyl)pyridin-4-yl]oxy}phenyl) |
| 41 | (thiazolo[5,4-d]pyrimidin-7-yl)-NH-CH₂CH₂-(3-fluoro-4-{[4-(trifluoromethyl)pyridin-2-yl]oxy}phenyl) |
| 42 | (thiazolo[5,4-d]pyrimidin-7-yl)-NH-CH₂CH₂-(3-methoxy-4-{[1-oxido-4-(trifluoromethyl)pyridin-2-yl]oxy}phenyl) |

TABLE 1-continued
Examples of compounds of formula (I-A) and (I-B).
| Compound | Structure |
|---|---|
| 43 | 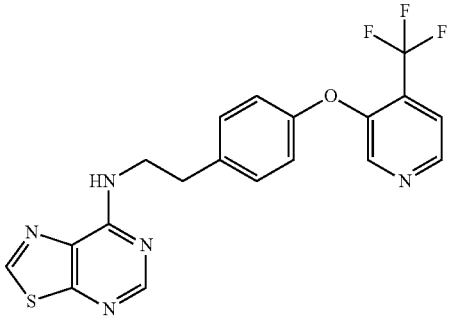 [SMILES: FC(F)(F)c1ccncc1Oc1ccc(CCNc2ncnc3scnc23)cc1] |
| 44 | 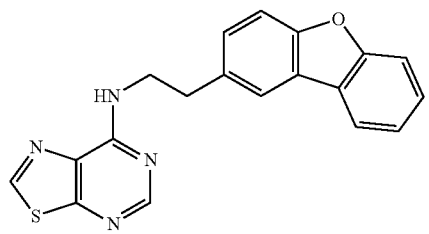 [SMILES: c1ccc2c(c1)oc1ccc(CCNc3ncnc4scnc34)cc12] |
| 45 | 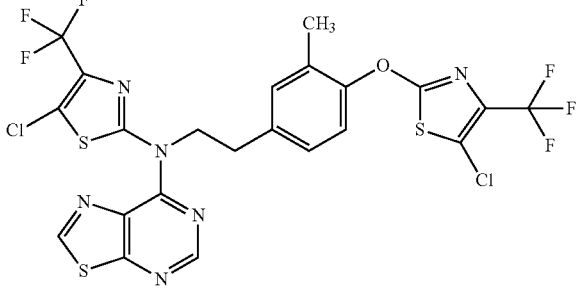 |
| 46 | 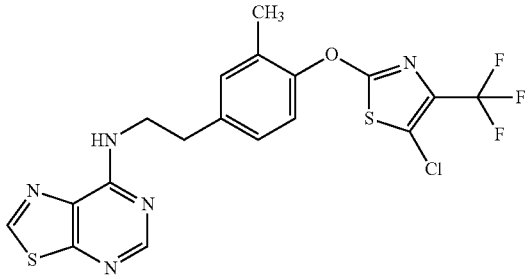 [SMILES: Cc1cc(CCNc2ncnc3scnc23)ccc1Oc1nc(C(F)(F)F)c(Cl)s1] |
| 47 | 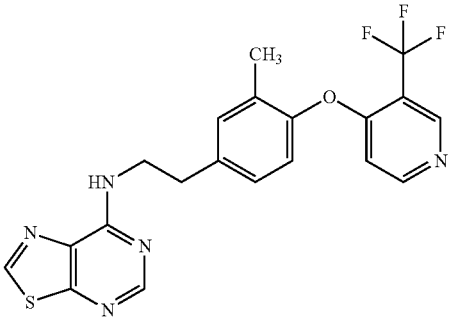 [SMILES: Cc1cc(CCNc2ncnc3scnc23)ccc1Oc1ccncc1C(F)(F)F] |

TABLE 1-continued
Examples of compounds of formula (I-A) and (I-B).
| Compound | Structure |
|---|---|
| 48 | 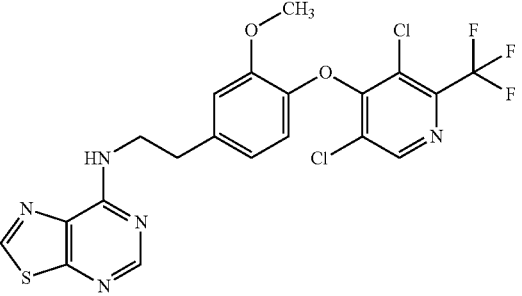 [SMILES: COc1cc(CCNc2ncnc3scnc23)ccc1Oc1c(Cl)cnc(C(F)(F)F)c1Cl] |
| 49 | 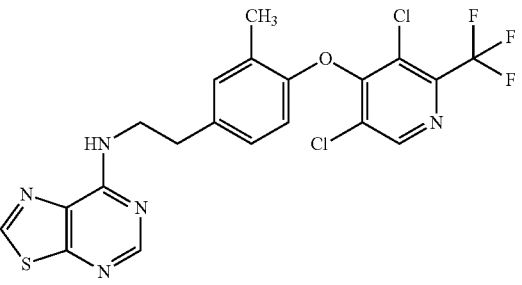 [SMILES: Cc1cc(CCNc2ncnc3scnc23)ccc1Oc1c(Cl)cnc(C(F)(F)F)c1Cl] |
| 50 | 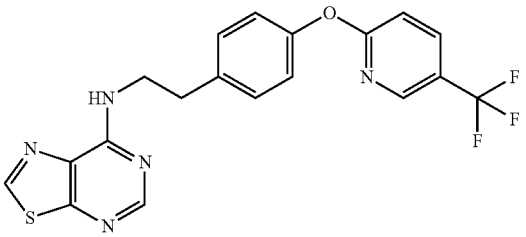 [SMILES: FC(F)(F)c1ccc(Oc2ccc(CCNc3ncnc4scnc34)cc2)nc1] |
| 51 | 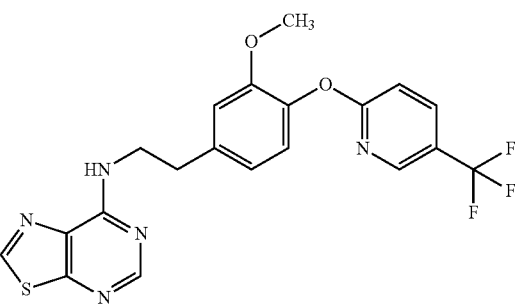 [SMILES: COc1cc(CCNc2ncnc3scnc23)ccc1Oc1ccc(C(F)(F)F)cn1] |
| 52 | 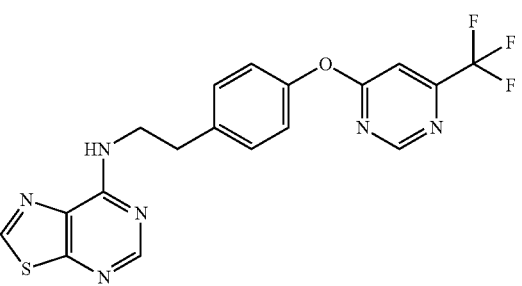 [SMILES: FC(F)(F)c1cc(Oc2ccc(CCNc3ncnc4scnc34)cc2)ncn1] |

TABLE 1-continued

Examples of compounds of formula (I-A) and (I-B).

| Compound | Structure |
|---|---|
| 53 | (structure) |
| 54 | (structure) |
| 55 | (structure) |
| 56 | (structure) |
| 57 | (structure) |
| 58 | (structure) |

TABLE 1-continued

Examples of compounds of formula (I-A) and (I-B).

| Compound | Structure |
|---|---|
| 59 | 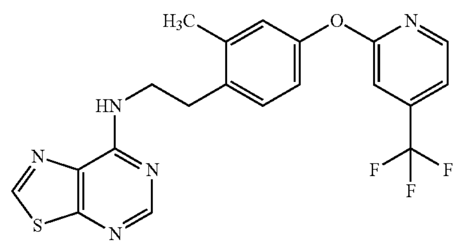 [SMILES: Cc1cc(Oc2cc(C(F)(F)F)ccn2)ccc1CCNc1ncnc2scnc12] |
| 60 | 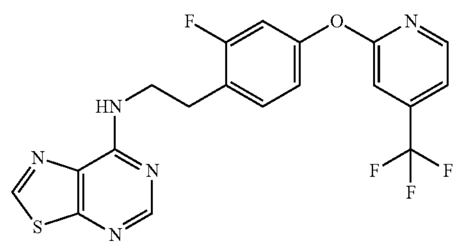 [SMILES: Fc1cc(Oc2cc(C(F)(F)F)ccn2)ccc1CCNc1ncnc2scnc12] |
| 61 | 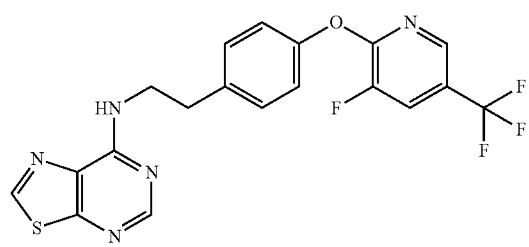 [SMILES: Fc1cc(C(F)(F)F)cnc1Oc1ccc(CCNc2ncnc3scnc23)cc1] |
| 62 | 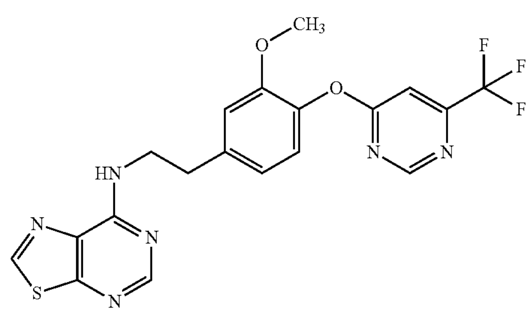 [SMILES: COc1cc(CCNc2ncnc3scnc23)ccc1Oc1cc(C(F)(F)F)ncn1] |
| 63 | 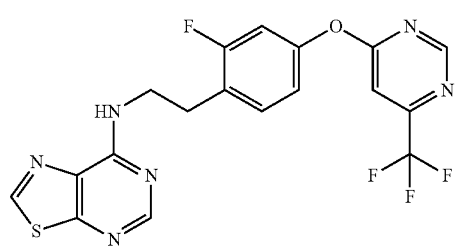 [SMILES: Fc1cc(Oc2cc(C(F)(F)F)ncn2)ccc1CCNc1ncnc2scnc12] |

TABLE 2

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 1 | 286 (GC-MS, m/z) | Example 1 | Suzuki, E.; Sugiura, S.; Naito, T.; Inoue, S. *Chem. & Pharm. Bull.* 1968, 16, 750. | (structure: 1-(4-methoxyphenyl)ethylamine) |
| 2 | 375.2 | Example 5 | Suzuki, E.; Sugiura, S.; Naito, T.; Inoue, S. *Chem. & Pharm. Bull.* 1968, 16, 750. | (structure: 2-(4-((4-cyanopyridin-2-yl)oxy)phenyl)ethylamine) |
| 3 | 273.1 | Example 1 | Suzuki, E.; Sugiura, S.; Naito, T.; Inoue, S. *Chem. & Pharm. Bull.* 1968, 16, 750. | (structure: 2-(4-hydroxyphenyl)ethylamine) |
| 4 | 356.2 | Example 6 | (pentafluoropyridine structure) | Dreikorn, B.A. et al., WO9404527 A1, 1994. (structure: 2-(6-(2,2,2-trifluoroethoxy)pyridin-3-yl)ethylamine) |
| 5 | 421 (M+) | Example 8 | (6-chloropyridine-2-carbonitrile structure) | 3 |
| 6 | 374 (M+) | Example 14 | (2-fluoro-4-(trifluoromethyl)pyridine structure) | 3 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 7 | 417 (M+) | Example 8 | Suzuki, E.; Sugiura, S.; Naito, T.; Inoue, S. *Chem. & Pharm. Bull.* 1968, 16, 750. 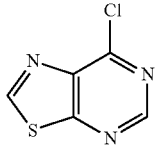 | 3 |
| 8 | 418.1 | Example 8 | 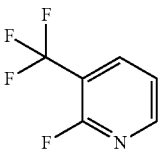 | 3 |
| 9 | 448.1 | Example 13 | 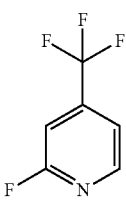 [SMILES: Fc1cc(C(F)(F)F)ccn1] | 22 |
| 10 | 314 (M+) | Example 3 | Suzuki, E.; Sugiura, S.; Naito, T.; Inoue, S. *Chem. & Pharm. Bull.* 1968, 16, 750. 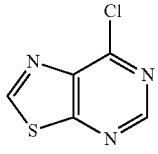 | As in Preparation 4, Step 3. 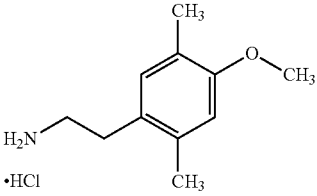 |
| 11 | 300 (M+) | Example 4 | 10 | |
| 12 | 303.1 | Example 2 | Suzuki, E.; Sugiura, S.; Naito, T.; Inoue, S. *Chem. & Pharm. Bull.* 1968, 16, 750. 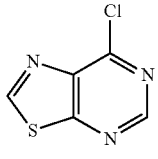 | 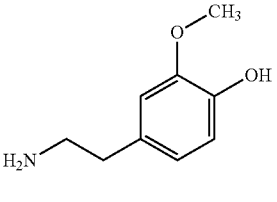 |
| 13 | 446 | Example 8 | 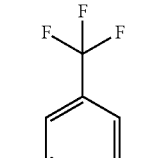 | 11 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 14 | 467.8 | Example 7b | Scovell, E. G.; Watson, D. J. EP63872A1, 1982. [structure: pentafluoro-trifluoromethyl pyridine] | 15 |
| 15 | yellow solid | Example 3 | Suzuki, E.; Sugiura, S.; Naito, T.; Inoue, S. *Chem. & Pharm. Bull.* 1968, 16, 750. [structure: 7-chlorothiazolo[5,4-d]pyrimidine] | [structure: 4-hydroxyphenyl isopropylamine · HBr] |
| 16 | 476.2 | Example 8 | [structure: methyl 6-chloro-4-(trifluoromethyl)nicotinate] | 3 |
| 17 | 447 (M+) | Example 8 | [structure: 2-fluoro-4-(trifluoromethyl)pyridine] | 12 |
| 18 | 432.5 | Example 8 | [structure: 2-fluoro-4-(trifluoromethyl)pyridine] | 15 |
| 19 | 300 (M+) | Example 3 | Suzuki, E.; Sugiura, S.; Naito, T.; Inoue, S. *Chem. & Pharm. Bull.* 1968, 16, 750. [structure: 7-chlorothiazolo[5,4-d]pyrimidine] | [structure: 3-methyl-4-methoxyphenethylamine · HCl] |
| 20 | 287 (M+) | Example 4 | 19 | |

TABLE 2-continued

Characterizing data (mass spectrometry or other), as well as preparative method, electrophile or
other reactant and amine or other reactant, for compounds of formula (I-A) and (I-B) in TABLE 1.

| Compound | ESIMS (m/z, [M + H +]) or Other Data | Preparative Method (Example Number) | Electrophile or Other Reactant (Compound Name, Structure, or Number) | Amine or Other Reactant (Compound Name, Structure or Number) |
|---|---|---|---|---|
| 21 | 364 (M+) | Example 3 | Suzuki, E.; Sugiura, S.; Naito, T.; Inoue, S. *Chem. & Pharm. Bull.* 1968, 16, 750. [structure: 4-chlorothiazolo[5,4-d]pyrimidine] | [structure: 3-bromo-4-methoxyphenethylamine] |
| 22 | 303.0 | Example 12 | Suzuki, E.; Sugiura, S.; Naito, T.; Inoue, S. *Chem. & Pharm. Bull.* 1968, 16, 750. [structure: 4-chlorothiazolo[5,4-d]pyrimidine] | Preparation 4 [structure with ·HCl] |
| 23 | 432 | Example 8 | [structure: 2-fluoro-4-(trifluoromethyl)pyridine] | 20 |
| 24 | 432.1 | Example 8 | [structure: 2-fluoro-3-(trifluoromethyl)pyridine] | 20 |
| 25 | 350.9, 352.9 | Example 4 | 21 | |
| 26 | 300 (M+) | Example 4 | 28 | |
| 27 | 554.1 | Example 8 | [structure: methyl 6-chloro-4-(trifluoromethyl)nicotinate] | 25 |
| 28 | yellow solid | Example 3 | Suzuki, E.; Sugiura, S.; Naito, T.; Inoue, S. *Chem. & Pharm. Bull.* 1968, 16, 750. [structure: 4-chlorothiazolo[5,4-d]pyrimidine] | As in Preparation 3. [structure with ·HCl] |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 29 | 447.9 | Example 8 | (3-fluoro-4-(trifluoromethyl)pyridine structure) | 12 |
| 30 | 465.2 | Example 10 | (3,4-difluoro-1-(trifluoromethyl)benzene structure) | 12 |
| 31 | 448.3 | Example 8 | (4-chloro-3-(trifluoromethyl)pyridine·HCl structure) | 12 |
| 32 | 484.5 | Example 7a | Scovell, E. G.; Watson, D. J. EP63872A1, 1982. (3,4,5-trifluoro-2-(trifluoromethyl)pyridine structure) | 12 |
| 33 | 453.9 | Example 7a | Scovell, E. G.; Watson, D. J. EP63872A1, 1982. (3,4,5-trifluoro-2-(trifluoromethyl)pyridine structure) | 3 |
| 34 | 273 | Example 6 | Suzuki, E.; Sugiura, S.; Naito, T.; Inoue, S. Chem. & Pharm. Bull. 1968, 16, 750. (4-chlorothiazolo[5,4-d]pyrimidine structure) | (4-(1-aminoethyl)phenol structure) |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 35 | 417.9 | Example 8 | [4-(trifluoromethyl)-2-fluoropyridine structure] | 34 |
| 36 | 454.1 | Example 7a | [4-(trifluoromethyl)-2,3,5-trifluoropyridine structure] | 3 |
| 37 | 448 (M+) | Example 7a | [4-amino-2,3,5,6-tetrafluoropyridine structure] | 12 |
| 38 | 305.0 | Example 6 | Suzuki, E.; Sugiura, S.; Naito, T.; Inoue, S. *Chem. & Pharm. Bull.* 1968, 16, 750. [4-chlorothiazolo[5,4-d]pyrimidine structure] | As in Preparation 3. [2-(3-fluoro-4-methoxyphenyl)ethylamine·HCl structure] |
| 39 | 290 (M+) | Example 4 | 38 | |
| 40 | 417 (M+) | Example 5 | Suzuki, E.; Sugiura, S.; Naito, T.; Inoue, S. *Chem. & Pharm. Bull.* 1968, 16, 750. [4-chlorothiazolo[5,4-d]pyrimidine structure] | [2-(4-((2-(trifluoromethyl)pyridin-4-yl)oxy)phenyl)ethylamine structure] |
| 41 | 435.9 | Example 8 | [4-(trifluoromethyl)-2-fluoropyridine structure] | 39 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
| --- | --- | --- | --- | --- |
| 42 | 464.1 | Example 8 | Preparation 6 | 12 |
| 43 | 418.2 | Example 11 | Suzuki, E.; Sugiura, S.; Naito, T.; Inoue, S. *Chem. & Pharm. Bull.* 1968, 16, 750. | As in Preparation 2 |
| 44 | 347.1 | Example 5 | Suzuki, E.; Sugiura, S.; Naito, T.; Inoue, S. *Chem. & Pharm. Bull.* 1968, 16, 750. | |
| 45 | 654.7 | Example 8 | | 20 |
| 46 | 472.1 | Example 8 | | 20 |
| 47 | 432.4 | Example 8 | | 20 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 48 | 516.1 | Example 8 | Fung, A. P.; Wilson, C. A.; Fujioka, G. S.; Werner, J. A. EP 110690 A1, 1984. | 12 |
| 49 | 500.1 | Example 8 | Fung, A. P.; Wilson, C. A.; Fujioka, G. S.; Werner, J. A. EP 110690 A1, 1984. | 20 |
| 50 | 418.2 | Example 8 | | 3 |
| 51 | 449.2 | Example 8 | | 12 |
| 52 | 419.2 | Example 8 | | 3 |
| 53 | 433.2 | Example 8 | | 20 |
| 54 | 449.3 | Example 8 | | 12 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 55 | 305.5 | Example 3 | Suzuki, E.; Sugiura, S.; Naito, T.; Inoue, S. *Chem. & Pharm. Bull.* 1968, 16, 750. [6-chlorothiazolo[5,4-d]pyrimidine structure] | Preparation 1 [3-fluoro-4-methoxyphenethylamine·HCl structure] |
| 56 | 301.2 | Example 3 | Suzuki, E.; Sugiura, S.; Naito, T.; Inoue, S. *Chem. & Pharm. Bull.* 1968, 16, 750. [6-chlorothiazolo[5,4-d]pyrimidine structure] | Preparation 3 [2-methyl-4-methoxyphenethylamine·HCl structure] |
| 57 | 286.9 | Example 4 | 56 | |
| 58 | 291.2 | Example 4 | 55 | |
| 59 | 432.3 | Example 8 | [2-fluoro-4-(trifluoromethyl)pyridine structure] | 57 |
| 60 | 436.3 | Example 8 | [2-fluoro-4-(trifluoromethyl)pyridine structure] | 58 |
| 61 | 436.3 | Example 8 | [2,3-difluoro-5-(trifluoromethyl)pyridine structure] | 3 |
| 62 | 432.2 | Example 9 | [2-fluoro-6-methyl-4-(trifluoromethyl)pyridine structure] | 3 |

TABLE 2-continued

Characterizing data (mass spectrometry or other), as well as preparative method, electrophile or other reactant and amine or other reactant, for compounds of formula (I-A) and (I-B) in TABLE 1.

| Compound | ESIMS (m/z, [M + H + ]) or Other Data | Preparative Method (Example Number) | Electrophile or Other Reactant (Compound Name, Structure, or Number) | Amine or Other Reactant (Compound Name, Structure or Number) |
|---|---|---|---|---|
| 63 | 436.8 | Example 8 | Cl-pyrimidine-CF$_2$F | 58 |

Biological Testing

Table 3 shows representative compounds of formula (I-A) and (I-B), together with characterizing biological data.

TABLE 3

Compounds of formula (I-A) and (I-B) and the biological activity against representative fungal diseases and insects.

| Compound | Activity against Fungal Diseases | | | | Activity against Insects |
|---|---|---|---|---|---|
| | PSPECU | PUCCRT | PYRIOR | SEPTTR | |
| 1 | NT | *** | *** | NT | – |
| 2 | NT | *** | *** | ** b | + |
| 3 | NT | * | * | * b | – |
| 4 | NT | *** | *** | * b | + |
| 5 | NT | *** a | NT | * b | NT |
| 6 | NT | NT | NT | NT | NT |
| 7 | *** | *** | *** | *** | + |
| 8 | *** | *** | *** | *** | + |
| 9 | *** | *** | *** | *** | – |
| 10 | NT | NT | NT | NT | NT |
| 11 | NT | NT | NT | NT | NT |
| 12 | NT | NT | NT | NT | NT |
| 13 | *** | *** | *** | *** | + |
| 14 | NT | * a | NT | *** b | + |
| 15 | NT | NT | NT | NT | NT |
| 16 | *** | *** | ** | ** | + |
| 17 | NT | *** a | NT | *** b | + |
| 18 | *** | *** | *** | *** | + |
| 19 | NT | *** | NT | ** | – |
| 20 | NT | * | NT | * | – |
| 21 | NT | NT | NT | NT | NT |
| 22 | NT | NT | NT | NT | NT |
| 23 | *** | *** | *** | *** | + |
| 24 | *** | *** | ** | *** | + |
| 25 | NT | NT | NT | NT | NT |
| 26 | NT | NT | NT | NT | NT |
| 27 | *** | *** | *** | ** | + |
| 28 | NT | NT | NT | NT | NT |
| 29 | NT | *** a | NT | ** b | NT |
| 30 | *** | *** | *** | *** b | + |
| 31 | ** | *** | *** | *** b | + |
| 32 | *** | *** | *** | *** b | + |
| 33 | *** | *** | *** | *** | + |
| 34 | NT | NT | NT | NT | NT |
| 35 | *** | *** | *** | *** | + |
| 36 | *** | *** | *** | *** | + |
| 37 | *** | *** | *** | *** | + |
| 38 | NT | NT | NT | NT | NT |
| 39 | NT | NT | NT | NT | NT |
| 40 | *** | *** | *** | *** | + |
| 41 | *** | *** | *** | *** | + |
| 42 | *** | *** | *** | *** | – |
| 43 | *** | *** | *** | *** | + |
| 44 | *** | * | *** | ** | – |
| 45 | NT | * a | NT | * b | NT |
| 46 | *** | *** | *** | *** | + |
| 47 | NT | *** | *** | *** | + |
| 48 | NT | *** | *** | *** | + |
| 49 | ** | ** | *** | * b | – |
| 50 | NT | *** a | NT | *** b | + |
| 51 | NT | *** a | NT | *** b | + |
| 52 | *** | *** | *** | *** b | + |
| 53 | *** | *** | *** | *** b | + |
| 54 | NT | *** | NT | *** | + |
| 55 | NT | *** | NT | * | + |
| 56 | NT | * | NT | ** | + |
| 57 | NT | * | NT | * | – |
| 58 | NT | * | NT | * | – |
| 59 | *** | *** | *** | *** | + |
| 60 | NT | *** | NT | *** | + |
| 61 | *** | *** | *** | ** b | + |
| 62 | *** | *** | *** | *** | + |
| 63 | NT | * | NT | * | + | a = Tested at 3 ppm
b = Tested at 25 ppm
NT = Not tested

Fungicide activity data are the level (in percent) at which the given disease was controlled when the given compound was applied to the foliage of the plants at 200 ppm. In a few cases (noted in the table) the compound was applied to the plants at 25 ppm or 3 ppm. The plants were inoculated with the fungus one day after treatment. *=80-100% control; =50-79% control; *=0-49% control.

Insect activity data: if any species was controlled at 80% or more, the compound was considered active. "+" indicates activity; "–" indicates lack of activity.

Fungicidal Activity

The compounds of the present invention have been found to have significant fungicidal effect, particularly for agricultural use. Many of the compounds are particularly effective for use with agricultural crops and horticultural plants. In particular, the compounds effectively control a variety of undesirable fungi that infect useful plant crops. Activity has been demonstrated for a variety of fungi, including for example the following representative fungi species: Downy Mildew of Cucumber (*Pseudoperonospora cubensis*—PSPECU), Rice Blast (*Pyricularia oryzae* PYRIOR), Brown Rust of Wheat (*Puccinia recondita tritici*—PUCCRT); *Septoria* Blotch of Wheat (*Septoria tritici*—SEPTTR).

It will be understood by those skilled in the art that the efficacy of the compounds against the foregoing fungi establishes the general utility of the compounds as fungicides. The activity of the compounds as effective fungicides was determined by applying the compounds to plants and observing control of fungal disease. The compounds were formulated at 200 parts per million (ppm) in 10 volume percent (vol %) acetone plus 90 vol % Triton X-100 water (deionized $H_2O$ 99.99 weight percent (wt %)+0.01 wt % Triton X100), giving a "formulated test compound." In a few cases, compounds were formulated at 25 ppm or 3 ppm rather than 200 ppm in 10 vol % acetone plus 90 vol % Triton X-100 water (deionized $H_2O$ 99.99 wt %+0.01 wt % Triton X100), giving a "formulated test compound." Formulated test compounds were applied to plants using a turntable sprayer fitted with two opposing air atomization nozzles which delivered approximately 1500 liters/hectare (L/ha) of spray volume.

All plants were inoculated with spores of the fungus the day after treatment, then incubated in an environment conducive to disease development. Disease severity was evaluated 4 to 25 days (d) later, depending on the speed of disease development. The following experiments were performed in the laboratory to determine the fungicidal efficacy of the compounds of the invention.

Leaf Rust of Wheat (causal agent *Puccinia recondita tritici=Puccinia triticina*; Bayer code PUCCRT): Wheat plants (variety 'Yuma') were grown from seed in a soil-less peat-based potting mixture (Metromix) until the seedlings had a fully expanded first leaf. Each pot contained 3-8 seedlings. These plants were sprayed until wet with the formulated test compounds. On the following day, the leaves were inoculated with an aqueous spore suspension of *Puccinia recondita tritici* and the plants were kept in high humidity overnight to permit spores to germinate and infect the leaf. The plants were then transferred to a greenhouse until disease developed on untreated control plants.

Cucumber Downy Mildew (causal agent *Pseudoperonospora cubensis*; Bayer code PSPECU): Cucumber plants (variety 'Bush Champion' or 'Bush Pickle Hybrid') were grown from seed in a soil-less peat-based potting mixture (Metromix) until the first true leaf was 20-80% expanded. Each pot contained 1 seedling. These plants were sprayed until wet with the formulated test compound. On the following day, the leaves were inoculated with an aqueous suspension of downy mildew sporangia and the plants were kept in high humidity for one day to permit sporangia to germinate and infect the leaf. The plants were then incubated in a growth chamber until disease developed on untreated control plants.

Rice Blast (causal agent *Magnaporthe grisea=Pyricularia oryzae*; Bayer code PYRIOR): Rice plants (variety 'M202') were grown from seed in a soil-less peat-based potting mixture (Metromix) until the seedlings had a partly to fully expanded second leaf. Each pot contained 5-20 seedlings. These plants were sprayed until wet with the formulated test compound. On the following day, the leaves were inoculated with an aqueous spore suspension of *Pyricularia oryzae* and the plants were kept in high humidity overnight to permit spores to germinate and infect the leaf. The plants were then transferred to a growth chamber until disease developed on untreated control plants.

*Septoria* Blotch of Wheat (causal agent *Septoria tritici=Mycosphaerella graminicola*; Bayer code SEPTTR): Wheat plants (variety 'Yuma') were grown from seed in a 50% pasteurized soil/50% soil-less mix until the seedlings had a fully expanded first leaf. Each pot contained 3-10 seedlings. These plants were sprayed until wet with the formulated test compound. On the following day, the leaves were inoculated with an aqueous spore suspension of *Septoria tritici* and the plants were kept in high humidity (one day in a dark dew chamber followed by two days in a lighted dew chamber) to permit spores to germinate and infect the leaf. The plants were then transferred to a greenhouse until disease developed on untreated control plants.

Table 3 presents the activity of typical compounds of the present invention when evaluated in these experiments. The effectiveness of the test compounds at controlling disease when sprayed on leaves was determined by assessing the severity of disease on treated plants, then converting the severity to percent control based on the level of disease on untreated, inoculated plants.

Insecticidal Activity

The compounds of the present invention have been found to have insecticidal activity. Activity may be demonstrated for a variety of insects, including for example the following representative insect species: Beet Armyworm (*Spodoptera exigua*—LAPHEG); Mosquito (*Aedes aegypti*—AEDSAE), Fruit Fly (*Drosophila melanogaster*—DROSME), and Green Peach Aphid (*Myzus persicae*—MYZUPE). It will be understood by those skilled in the art that the efficacy of the compounds against the foregoing insects establishes the general utility of the compounds as insecticides.

The activity of the compounds as effective insecticides was determined by applying the compounds to diet, plants or $H_2O$, placing insects in the $H_2O$ or on the diet (aphids are placed on plants prior to application) and observing mortality after an appropriate incubation time. The compounds were formulated at 4000 ppm in DMSO giving a "formulated test compound." Formulated test compounds were diluted in 96-well plates with acetone-$H_2O$ solutions and applied to species-specific diet or $H_2O$. The plates were infested and evaluated as described below. Results were averaged over 2-6 replications.

DROSME: Formulated test compounds were applied to microtiter plates containing fruit fly agar (10% sugar/$H_2O$) to give a dose of 80 µg test compound/well. Plates were infested by placing at least three flies in each well and sealing the plate. Mortality was evaluated after incubation for two days at room temperature.

AEDSAE: Plates containing formulated test compounds at 6 µg per well were diluted with $H_2O$ containing mosquito larvae. Each well contained at least two larvae. Mortality was evaluated after incubation for three days at room temperature.

LAPHEG: Formulated test compounds were applied to 96-well plates containing Lepidoptera diet at 12 µg per well. Plates were infested by placing at least four fresh armyworm eggs in each well and sealing the plate with cotton batting and plastic. Mortality was evaluated after incubation for seven days at 28° C.

MYZUPE: Test compounds were dissolved in 50:50 methanol-ethanol and diluted in 0.025% (v/v) Tween 20/$H_2O$ to a concentration of 200 ppm, generating a "formulated test compound" for plant application. The final concentration of solvents was 20%. Formulated test compounds were sprayed onto leaves of cabbage plants ('Early Jersey Wakefield') infested with green peach aphids. Plants were held in a controlled environment room at approximately 26° C. with 16 h of light. Mortality was evaluated after three days.

Table 3 presents the activity of typical compounds of the present invention when evaluated in these experiments. The effectiveness of the test compounds at controlling insects was determined by assessing the mortality on treated test plates or plants, then converting the average mortality to percent control. If any of the species—DROSME, AEDSAE, MYSUPE or LAPHEG—was controlled at 80% or more, the compound was considered active (shown as "+" in Table 3). If no species was controlled at 80% or more, the compound was considered inactive (shown as "−" in Table 3).

Animal Health Activity

The compounds of the present invention have been found to have significant potential as parasiticides for animal health. Table 4, shown below, presents the activity of typical compounds of the present invention when evaluated in these experiments. Activity has been demonstrated by three out of four compounds screened against *Caenorhabditis elegans*, a free-living nematode that is an indicator species for animal parasites. It will be understood by those skilled in the art that the efficacy of three compounds against *Caenorhabditis elegans*, which at 10 μg/mL was equivalent to the commercial parasiticide product ivermectin, establishes the potential utility of these compounds to control parasites that attack animals.

The activity of the compounds against *Caenorhabditis elegans* was determined by dissolving compounds in DMSO, then applying them to petri dishes containing Nematode Growth Medium agar to a final concentration of 10 micrograms (μg) compound per milliliter agar. *Escherichia coli* bacteria were grown on the plates to provide a food source for the larvae of *Caenorhabditis elegans*. The bacteria were heat-killed at 65° C. before compounds were added to the plates.

The plates with compound and heat-killed bacteria were infested with 10 microliter (μL) drops containing eggs from wild-type *Caenorhabditis elegans* worms. Adult worms were dissolved in potassium hydroxide (KOH) and bleach and washed in Ringers solution to generate the egg suspension. Each compound was screened with approximately 400 eggs, divided between two petri dishes. Egg hatching was evaluated after 24 h at 20° C. Mortality was averaged over the two plates.

TABLE 4

Activity of compounds of the formula (I-A) and (I-B) against *Caenorhabditis elegans*.

| Compound | Percent mortality |
|---|---|
| 2 | 100 |
| 4 | 100 |
| 35 | 5 |
| 43 | 100 |
| Ivermectin | 95 |
| Untreated | <2 |

Application rate is 10 micrograms per milliliter agar.

The invention claimed is:

1. A compound of Formula (I-A):

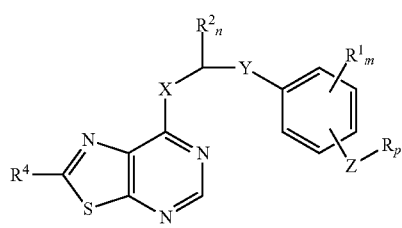

I-A wherein:
R is H, lower alkyl, phenyl, pyridine N-oxide, or a heterocycle comprising a 5 or 6 membered single ring, wherein the lower alkyl, phenyl, pyridine N-oxide, or 5 or 6 membered single ring heterocycle are optionally substituted with halo, lower alkyl, lower alkoxy, benzyloxy, lower alkenyl, lower alkynyl, haloalkyl, haloalkoxy, $NO_2$, CN, lower alkoxycarbonyl, lower alkanoyl, lower alkyl-$SO_q$, and aldoximes and lower alkyloximes optionally substituted on oxygen by lower alkyl;

Z is a single bond between the phenyl ring and a carbon atom of R, $CH_2$, NH, O, S, $CH_2O$, $OCH_2$, $CH_2CH_2$, or $OCH_2CH_2$;

m is 4;

p is 0 or 1;

q is an integer from 0 to 2;

$R^1$ is independently H, halo, lower alkyl, lower alkenyl, lower alkynyl, hydroxy, lower alkoxy, haloalkyl, haloalkoxy, $NO_2$, CN, lower alkanoyl, lower alkoxycarbonyl, mercapto, lower alkylthio, aldoximes and lower alkyloximes optionally substituted on oxygen by lower alkyl;

Y is a single bond, $C((R^5)_n)O$ or $C((R^5)_n)$;

n is 2;

$R^2$ are independently H or lower alkyl;

$R^4$ is H, halogen, lower alkyl, lower alkoxy or lower haloalkyl;

$R^5$ are independently H or lower alkyl; and

X is $NR^3$, or O, where $R^3$ is selected from H, lower alkyl, lower alkanoyl, lower alkoxycarbonyl, hydroxy, lower alkoxy, lower alkyl-$SO_q$, phenyl-$SO_q$ or substituted phenyl-$SO_q$.

2. The compound of claim 1, wherein $R^3$ and $R^4$ are H and X is $NR^3$.

3. The compound of claim 2, wherein Y is $C((R^5)_n)$.

4. The compound of claim 3, wherein $R^1$ is H, lower alkyl, lower alkoxy, or halo.

5. The compound of claim 4, wherein Z is O and p is 1.

6. The compound of claim 5, wherein R is an N containing 5 or 6 membered single ring optionally substituted with halo, lower alkyl, and haloalkyl.

7. The compound of claim 2, wherein Y is a single bond, Z is O and p is 1.

8. The compound of claim 7, wherein $R^1$ is H, lower alkyl, lower alkoxy, or halo.

9. The compound of claim 7, wherein R is an N containing 5 or 6 membered single ring optionally substituted with halo, lower alkyl, and haloalkyl.

10. The compound of claim 2, wherein Y is a $C((R^5)_n)O$.

11. The compound of claim 10, wherein $R^1$ is H, lower alkyl, lower alkoxy, or halo.

12. The compound of claim 11, wherein Z is O and p is 1.

13. The compound of claim 12, wherein R is an N containing 5 or 6 membered single ring optionally substituted with halo, lower alkyl, and haloalkyl.

14. A process of controlling insects, parasites, and/or fungi, said process comprising applying a compound according to claim 1 to an area where control of insects, parasites, and/or fungi is desired.

15. A composition comprising a mixture of a compound according to claim 1 with at least one other pesticide.

16. A composition comprising a compound according to claim 1 and at least one of antimicrobials, bactericides, defoliants, safeners, synergists, algaecides, attractants, desiccants, pheromones, repellants, avicides, disinfectants, semiochemicals, or molluscicides.

17. A compound of Formula (I-B):

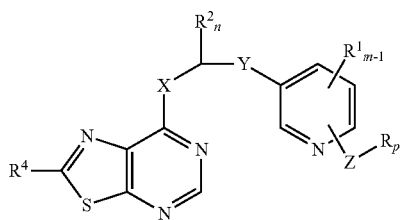

wherein:
  R is H, lower alkyl, phenyl, pyridine N-oxide, or a heterocycle comprising a 5 or 6 membered single ring, wherein the lower alkyl, phenyl, pyridine N-oxide, or 5 or 6 membered single ring heterocycle are optionally substituted with halo, lower alkyl, lower alkoxy, benzyloxy, lower alkenyl, lower alkynyl, haloalkyl, haloalkoxy, $NO_2$, CN, lower alkoxycarbonyl, lower alkanoyl, lower alkyl-$SO_q$, aldoximes and lower alkyloximes optionally substituted on oxygen by lower alkyl;
  Z is H, a single bond between the phenyl ring and a carbon atom of R, $CH_2$, NH, O, S, $CH_2O$, $OCH_2$, $CH_2CH_2O$, or $OCH_2CH_2$;
  m is 4;
  p is 0 or 1;
  q is an integer from 0 to 2;
  $R^1$ is independently H, halo, lower alkyl, lower alkenyl, lower alkynyl, hydroxy, lower alkoxy, haloalkyl, haloalkoxy, $NO_2$, CN, lower alkanoyl, lower alkoxycarbonyl, mercapto, lower alkylthio, aldoximes and lower alkyloximes optionally substituted on oxygen by lower alkyl;
  Y is a single bond, $C((R^5)_n)O$ or $C((R^5)_n)$;
  n is 2;
  $R^2$ are independently H or lower alkyl;
  $R^4$ is H, halogen, lower alkyl, lower alkoxy or lower haloalkyl;
  $R^5$ are independently H or lower alkyl; and
  X is $NR^3$, O, and S, where $R^3$ is selected from H, lower alkyl, lower alkanoyl, lower alkoxycarbonyl, hydroxy, lower alkoxy, lower alkyl-$SO_q$, phenyl-$SO_q$ or substituted phenyl-$SO_q$.

18. The compound of claim 1, wherein the compound is:

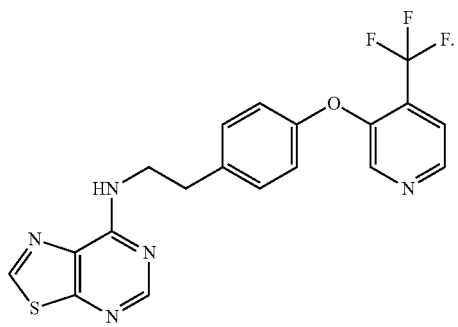 [SMILES: FC(F)(F)c1ccncc1Oc1ccc(CCNc2ncnc3scnc23)cc1]

19. The compound of claim 1, wherein Z is O and p is 1.

20. The compound of claim 19, R is an N containing 5 or 6 membered single ring optionally substituted with halo, lower alkyl, and haloalkyl.

* * * * *